(12) United States Patent
Lieblich et al.

(10) Patent No.: US 7,345,478 B2
(45) Date of Patent: Mar. 18, 2008

(54) METHOD AND APPARATUS FOR DETECTION OF QUADRUPOLE NUCLEI IN MOTION RELATIVE TO THE SEARCH REGION

(75) Inventors: David Lieblich, Worcester, MA (US); Jeffrey Schiano, State College, PA (US)

(73) Assignee: SIV Technologies, Inc., Cherry Valley, MA (US)

( * ) Notice: Subject to any disclaimer, the term of this patent is extended or adjusted under 35 U.S.C. 154(b) by 0 days.

(21) Appl. No.: 11/031,454

(22) Filed: Jan. 7, 2005

(65) Prior Publication Data

US 2008/0018332 A1 Jan. 24, 2008

Related U.S. Application Data

(60) Provisional application No. 60/534,886, filed on Jan. 7, 2004.

(51) Int. Cl.
G01V 3/00 (2006.01)
(52) U.S. Cl. .................................. 324/300; 324/307
(58) Field of Classification Search ......... 324/300–322
See application file for complete search history.

(56) References Cited

U.S. PATENT DOCUMENTS

| | | | |
|---|---|---|---|
| 4,514,691 A | 4/1985 | De Los Santos et al. ... | 324/301 |
| 5,159,617 A | 10/1992 | King et al. .................... | 378/57 |
| 5,168,224 A | 12/1992 | Maruizumi et al. ......... | 324/300 |
| 5,206,592 A | 4/1993 | Buess et al. ................. | 324/307 |
| 5,229,722 A | 7/1993 | Rommel et al. ............. | 324/307 |
| 5,233,300 A | 8/1993 | Buess et al. ................. | 324/307 |
| 5,323,004 A | 6/1994 | Ettinger et al. ........... | 250/336.1 |
| 5,365,171 A | 11/1994 | Buess et al. ................. | 324/307 |
| 5,457,385 A | 10/1995 | Sydney et al. .............. | 324/301 |
| 5,583,437 A * | 12/1996 | Smith et al. ................. | 324/307 |
| 5,592,083 A | 1/1997 | Magnuson et al. ......... | 324/300 |
| 5,594,338 A | 1/1997 | Magnuson ................... | 324/318 |
| 5,608,321 A | 3/1997 | Garroway et al. .......... | 324/307 |
| 5,804,967 A | 9/1998 | Miller et al. ................ | 324/314 |
| 5,814,989 A | 9/1998 | Smith et al. ................. | 324/300 |
| 5,986,455 A | 11/1999 | Magnuson ................... | 324/318 |
| 6,088,423 A | 7/2000 | Krug et al. ................... | 378/57 |
| 6,100,688 A | 8/2000 | Smith et al. ................. | 324/300 |

(Continued)

FOREIGN PATENT DOCUMENTS

EP 1 486 794 12/2004

(Continued)

*Primary Examiner*—Brij Shrivastav
(74) *Attorney, Agent, or Firm*—Weingarten, Schurgin, Gagnebin & Lebovici LLP

(57) ABSTRACT

A method and apparatus for detecting quadrupole nuclei in motion relative to a search region, during the sensing operation, provides a system for decreasing the throughput time of quadrupole resonance (QR) detection systems. The apparatus uses a single QR probe, or a plurality of QR probes, which may be formed into an array, to remotely and non-invasively generate a QR response from one or more targets containing quadrupole nuclei, as they pass through the probe-sensing region. The method employs an optimized pulse sequence that simultaneously increases the QR signal power while reducing the peak power of the RF pulses. The pulse sequence generates a matrix of signals that are processed to improve detection performance by increasing the signal to noise ratio.

50 Claims, 15 Drawing Sheets

U.S. PATENT DOCUMENTS

| | | | |
|---|---|---|---|
| 6,150,816 A | 11/2000 | Srinivasan | 324/318 |
| 6,194,898 B1 | 2/2001 | Magnuson et al. | 324/300 |
| 6,208,136 B1 * | 3/2001 | Smith et al. | 324/300 |
| 6,242,918 B1 | 6/2001 | Miller et al. | 324/322 |
| 6,291,994 B1 * | 9/2001 | Kim et al. | 324/300 |
| 6,392,408 B1 * | 5/2002 | Barrall et al. | 324/300 |
| 6,486,838 B1 * | 11/2002 | Smith et al. | 343/703 |
| 6,566,873 B1 * | 5/2003 | Smith et al. | 324/300 |
| 6,577,128 B1 | 6/2003 | Smith et al. | 324/309 |
| 2002/0093335 A1 | 7/2002 | Miller et al. | 324/309 |
| 2002/0153891 A1 | 10/2002 | Smith et al. | 324/309 |
| 2003/0001570 A1 | 1/2003 | Buess et al. | 324/307 |
| 2003/0071619 A1 | 4/2003 | Sauer et al. | 324/307 |

FOREIGN PATENT DOCUMENTS

| | | |
|---|---|---|
| JP | 06249807 | 9/1994 |
| WO | WO 2004/001545 | 12/2003 |

* cited by examiner

Phase Cycled SLSE/CPMG

Phase Cycled SORC (NPAPs-PAPs)

SORC

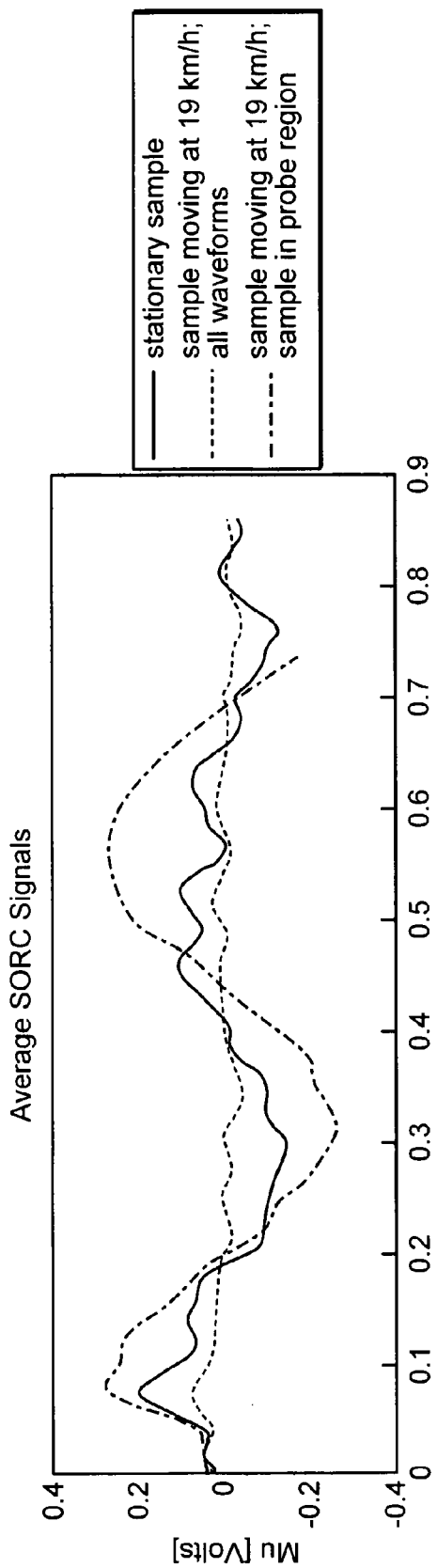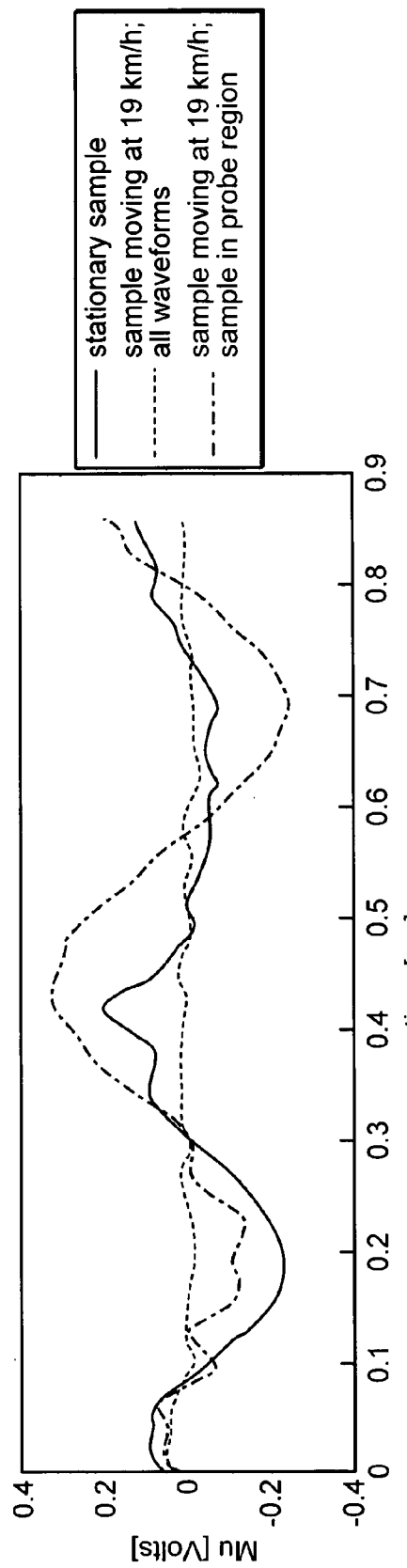

METHOD AND APPARATUS FOR DETECTION OF QUADRUPOLE NUCLEI IN MOTION RELATIVE TO THE SEARCH REGION

CROSS REFERENCE TO RELATED APPLICATIONS

This application claims priority to U.S. Application No. 60/534,886 filed on Jan. 7, 2004, the entire contents of this application being incorporated herein by reference.

BACKGROUND OF THE INVENTION

The interception of contraband, such as explosives, narcotics, and biological warfare agents, is an important issue in the effort to ensure public safety. Numerous technologies have been proposed to detect contraband, with each technology presenting its own set of strengths and weaknesses. It is desirable to quantify the detection performance of each technology to judge its viability. Of particular interest is the time required to search a specified region while maintaining a specified minimum probability of correct detection (PCD) and a specified maximum probability of false alarm (PFA). In order to achieve a desired PCD for an acceptable PFA, it is often useful to increase the search time, thereby limiting the throughput time through the search region. Overcoming environmental factors, which adversely affect the PCD, or noise, which may increase the PFA, can lead to further increases in search time. For example, although x-ray CAT-scan equipment is commonly used to inspect for contraband, these instruments generally take about 10 seconds to perform a scan. In addition, because standard x-ray instrumentation relies on indirect information such as shape and density, it generally cannot directly identify contraband material. Particularly problematic are sheet explosives. The ambiguity inherent in indirect detection produces degraded performance through increased PFA, which increases throughput time, and a decreased PCD, which allows contraband to pass through the screening procedure, in comparison to direct detection methods which have reduced ambiguity. Another commonly used method of detection is vapor-based or particulate trace-chemical analysis. Although these instruments are significantly less expensive and smaller than x-ray based systems, their performance is degraded by a large PFA because of their sensitivity to trace quantities. These systems typically perform analyses in seconds and either require physical contact with the scanned item, or a specially designed vapor capture method that disrupts the normal flow of activities.

SUMMARY OF THE INVENTION

The invention relates generally to bulk substance detection systems that reveal the presence of objects containing quadrupole nuclei, for example, contraband such as explosives, narcotics, or biological weapons. More particularly, the invention relates to an apparatus and method for remotely detecting such concealed substances while they are moving relative to the probe, with detection being accomplished by nuclear quadrupole resonance (QR) or nuclear magnetic resonance.

This invention provides a practical apparatus and method for QR detection of objects containing quadrupolar nuclei, which may be concealed, and are in controlled or uncontrolled motion, including constant or non-uniform velocity, through the probe-sensing region, during sensing. More specifically, the invention provides a system that improves the efficiency of a scanning operation wherein quadrupolar nuclei are detected, by permitting the normal flow of activities during scanning, as for example; scanning baggage as it moves on a conveyor belt for contraband, scanning humans for contraband as they walk through a portal, scanning for contraband by moving a handheld or other probe with respect to a sample to be investigated, as in scanning for mines, scanning humans for contraband, and scanning for biological materials. Efficiency improvements from increases in throughput are supplemented by improved effectiveness of the scanning operation wherein the probability of detection for the minimal threshold quantity of a quadrupolar material is increased, while the probability of false alarm is minimized.

A preferred embodiment of the invention utilizes a pulse sequence that is non-phase cycled. A non-phase cycled pulse sequence is a sequence in which the phase of the sequence has a constant or alternating phase within a given cycle and will have an equivalent phase in at least a pair of adjoining cycles. Alternatively the phase can be variable within a cycle, but at least a pair of cycles within the sequence will undergo the same change in phase.

A preferred embodiment of the apparatus includes one or more RF excitation loops with corresponding Q-damping loops and one or more reception loops with corresponding Q-damping loops as well as shielding designed to diminish ambient EM and RF noise. Multiple QR excitation and sensing loops can extend the probe-sensing region, thereby increasing the number of QR responses available for measurement, or they may only provide enhanced noise cancellation. Sensing the scan-item with multiple reception loops can be used to provide directional sensitivity and also provides a system for reducing the effects of AM-broadcast interference, piezoelectric ringing, and magnetoacoustic ringing. The loops can be composed of a metallic conductor, as is commonly used in practice, or they may be composed of a superconducting material. RF excitation at the loop(s) is achieved by generation of RF pulses from a pulse sequence synthesizer coupled to a pulse amplifier. A master oscillator provides timing for the entire system and provides an RF source for the pulse sequence synthesizer. Sensing is achieved by amplifying QR-response(s), received at the loop(s), and passing it (them) through a quadrature phase receiver(s). Analog signals, at the baseband frequency, from the quadrature phase receiver(s) are digitized. Digitization and processing take place in the data acquisition, processing and control module, which is PC-based. Detection cueing and conveyor stop/start are part of the control module.

A preferred method consists of detecting a possibly concealed quadrupolar object in motion through the probe-sensing region during the sensing operation by using a pulse sequence tailored to the QR response from moving quadrupolar targets and such that is, produces QR responses, as long as the sample remains within the probe-sensing region during excitation and sensing. In addition to a pulse sequence tailored to moving quadrupolar targets, the present invention addresses the problem that successive responses from moving quadrupolar targets have motion induced phase shifts, which can destroy coherent time-domain superposition of successive responses, and thus not only fail to achieve an enhancement of signal-to-noise ratio (SNR) but possibly degrade SNR. The present invention provides methods to effectively enhance the signal, by processing the multiple responses prior to superposition.

Tailoring the pulse sequence entails consideration of the multidimensional dependence of output signal response on input pulse parameters, external environmental parameters, and quadrupolar target parameters, including maximum velocity. A Transit Optimized Pulse Sequence (TOPS) results from the static maximization of output response as a function of these parameters, and/or the dynamic maximization as a function of their temporal variability. TOPS is designed to achieve detection of quadrupolar targets moving through a probe sensing region. In dynamic adjustment, successive responses are compared in a feedback algorithm that alters the pulse parameters to optimize the QR-response and provides the optimized parameters to the pulse sequence synthesizer, which tunes one or more excitation loops to, or near, the QR-resonance frequency(ies) of interest. Specifically, the pulse sequence is adjusted with respect to pulse width ($t_p$), pulse separation ($\tau$), and offset frequency ($\Delta f$), while accounting for the constraint of target transit time ($t_t$), through the probe-sensing region, to improve the SNR per unit time. Further adjustment of the pulse sequence with respect to input pulse power is achieved by recognizing that the maximum output power is not achieved at the maximum input power but that the output power is a nonlinear function of the input power and that this function is maximized at a specific power level which is a function of the input pulse-sequence parameters, the quadrupolar sample parameters, and external environmental parameters. Adjustment of the excitation frequency is achieved by adjusting the frequency in a feedback loop where the output signal, at the resonance offset frequency, is used to iteratively move the input frequency closer to resonance. The loop terminates when the output power is maximized, corresponding to minimization of offset error, under the conditions of a given experiment. This reduces the sensitivity of the QR measurement SNR to temperature variations of the quadrupolar nuclei. The result is a TOPS.

Processing received QR responses to enhance SNR is achieved by filtering and summing across the magnitude spectra, to coherently add successive responses without motion-induced phase shifts. The magnitude spectra (or the optional 1D magnitude spectrum) are used to derive a signal metric, within the region of the predetermined QR-resonance, and the noise metric is determined throughout the frequency spectrum. Such metrics can be defined using standard deterministic or statistical methods, such as the calibrated or mean amplitude of the signal response, which has been repeatedly measured, and the measured maximum noise or standard deviation of the noise response, respectively. If the signal metric exceeds a predetermined threshold and the noise metric is below a predetermined threshold, detection is indicated by visual and audible signals. Likewise, when detection is not present, or the response provides inconclusive or ambiguous information, different visual and audible signals are provided.

BRIEF DESCRIPTION OF THE SEVERAL VIEWS OF THE DRAWINGS

FIGS. 10a and 10b show a comparison of quadrupole signals in the time domain from a stationary quadrupolar target with fill factor 14%, and the same target moving at 12 mph (19 kph) through the probe sensing region.

DETAILED DESCRIPTION OF THE INVENTION

Figure 1A:
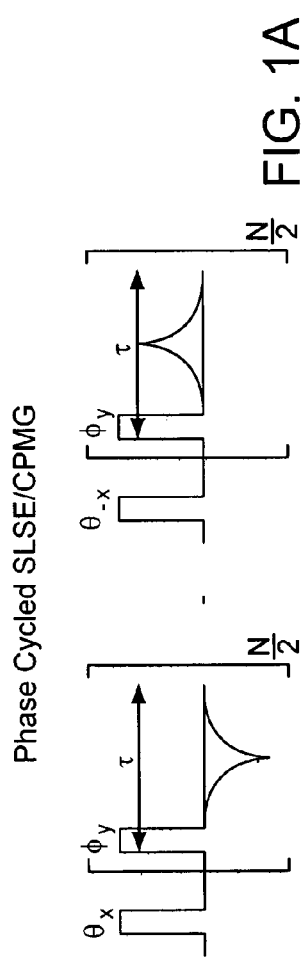
FIG. 1a illustrates the phase cycled SLSE/CPMG pulse sequences.

It is an object of the present invention to increase the throughput rate of QR detection systems by providing a method of remotely detecting, possibly concealed, quadrupolar targets as they move through one or more probe-sensing regions. It is a further object of the present invention to provide an apparatus for remotely detecting, possibly concealed, quadrupolar targets as they move continuously past one or more probe-sensing regions. By allowing the scanned object to move relative to the probe-sensing region, during the detection interval, the throughput time of a QR detection system can be substantially reduced, while simultaneously increasing the number of QR signals obtained for averaging, thereby increasing the SNR.

This method provides a significant increase in throughput rate by not disrupting the normal flow of scan-items such as: people, baggage, fluids carrying quadrupolar materials, or other containers of quadrupolar substances through the probe sensing region. This is a key consideration in such important applications as explosives and narcotics detection at airports. For example, current technology typically requires multiple seconds to scan a stationary object or scan-item. In contrast, the present invention can scan multiple scan-items in parallel while they move at velocities determined by normal practices, such as the speed of baggage conveyors at airports. The maximum velocity at which detection is possible is limited by the time the scan-item is within the probe sensing region, the size of the scan-item, the pulse rate, and the ambient noise. For example, detection of scan-items moving at over 12 mph can be performed for even a few grams of quadrupolar substance that occupy a few percent of the probe sensing region, using RF pulses with amplitudes on the order of a few Gauss at the material being scanned.

Quadrupole resonance (QR) detection systems directly detect bulk contraband such as explosives (RDX and TNT) and narcotics (Cocaine and Heroin), and are therefore capable of achieving a high PCD for a low PFA. The physical basis for QR detection is the electrical properties of atomic nuclei and their surrounding electronic environment. Atomic nuclei possessing both an electric quadrupole moment and a magnetic dipole moment are referred to as quadrupolar nuclei. If a quadrupolar nucleus experiences a non-zero electric-field gradient tensor due to the surrounding electronic charges, the resulting electrostatic interaction energy results in preferred orientations of the nucleus. The present system can perturb the orientation of quadrupolar nuclei by subjecting them to an external RF magnetic field at a frequency, also known as the resonant or transition frequency, determined by the energy difference between preferred orientations. As the resonant frequency is strongly dependent on the electric field gradient tensor, different chemical compounds containing the same quadrupolar nuclei will have distinct resonant frequencies. As an example, Table 1 shows the resonant frequencies associated with different explosive materials containing nitrogen-14 quadrupolar nuclei, at room temperature, along with the relaxation and decay times associated with each transition.

TABLE 1

| Compound | QR Resonance Frequency (MHz) | T1 (ms) | T2 (ms) | Linewidth (kHz) |
|---|---|---|---|---|
| TNT $v_+$ | 0.8701 | 4000 | 20-50 | 0.5 |
|  | 0.8589 | 3000 |  | 1.3 |
|  | 0.8481 | 9600 |  | 0.4 |
|  | 0.8438 | 4700 |  | 0.6 |
|  | 0.8422 | 3500 |  | 0.6 |
|  | 0.8366 | 2100 |  | 0.9 |
| TNT $v_-$ | 0.7683 | 9800 | 20-60 | 0.7 |
|  | 0.7509 | 2200 |  | 0.7 |
|  | 0.7426 | 3000 |  | 0.4 |
|  | 0.7395 | 5500 |  | 1.0 |
|  | 0.7140 | 4300 |  | 0.7 |
| RDX $v_+$ | 5.240 | 12 | 7.1 | 0.4 |
|  | 5.192 | 13 | 8.2 | 0.2 |
|  | 5.047 | 13 | 6.8 | 0.4 |
| RDX $v_-$ | 3.458 | 12 | 5.7 | 0.5 |
|  | 3.410 | 11 | 6.2 | 0.3 |
|  | 3.359 | 15 | 6.3 | 0.4 |
| HMX $v_-$ | 3.737 | ≈12000 | 125 | 1.4 |
|  | 3.623 | ≈9000 | 159 | 2.3 |
| PETN $v_+$ | 0.890 | ≈32000 | 50-60 | 0.3 |

A QR system detects a chemical compound by revealing the presence of quadrupolar nuclei contained within the compound. This is accomplished by applying a series of RF magnetic field pulses across a search region, at, or near, a resonant frequency of the quadrupolar nuclei. In between RF pulses the quadrupolar nuclei rotate back towards their preferred orientations. The rotating nuclear magnetic dipole moments induce a voltage in a pickup coil located within the search region, revealing the presence of the quadrupolar nuclei.

In comparison to other detection technologies, QR systems offer several advantages; namely (i) a QR detection system identifies a contraband component remotely, through its RF response, based on its resonant frequencies; (ii) because each compound has a unique set of resonant frequencies; benign materials do not produce false alarms, essentially eliminating a significant problem with other methods; (iii) QR systems detect bulk quantities of contraband, and as a result, are less prone to degradation by ambient "chemical noise" than trace chemical analyses; and (iv) as the contraband material must be located within a well-defined sensing region, QR detection systems provide information on the relative location of the contraband.

A significant challenge in the development of QR detection systems is a low signal-to-noise ratio (SNR) due to the small energy differences between the preferred orientations of the quadrupolar nuclei. A low SNR results in missed detections and false alarms. The most common method for increasing SNR is to coherently add consecutive QR signals produced by a multi-pulse sequence (see R. A. Marino and S. M. Klainer, Multiple Spin Echoes in Pure Quadrupole Resonance, J. Chem. Phys. 67(7), 3388-3389, 1978 and, S. S. Kim, J. R. P. Jayakody, and R. A. Marino, Experimental Investigations of the Strong-Off Resonant Comb (SORC) Pulse Sequence in $^{14}$N NQR, Zeitschrift fur Naturforschung A: Journal of Physical Sciences, 47A, 415-420, 1992, incorporated herein by reference). Coherent addition of the individual steady state QR responses increases the SNR, when the noise is random, by the square root of the number of signals averaged at the expense of increasing the search time.

Multi-pulse sequences used in existing QR detection systems are based on the Carr-Purcell-Meiboom Gil (CPMG) sequence, the spin-locked spin-echo sequence (SLSE), or the strong-off resonant comb (SORC) sequence. These sequences are referred to as steady state free precession sequences as the magnetization achieves a steady state after some time, t, that is generally at least two $T_1$. The CPMG sequence is represented as $$90_x - \frac{\tau}{2} - [180_y - \tau]_N, \qquad (1)$$

where 90 denotes a 90° pulse, x denotes that the pulse is applied along the x-axis, in a rotating frame, and τ is the delay between the 180° re-phasing pulses. When the pulse sequence is applied to a powder, instead of a single crystal, the meaning of the notation becomes symbolic rather than literal: the spread of crystal orientations causes the first maximum of magnetization to lie beyond 90°, and the corresponding first minimum to lie beyond 180°. The subsequence $\lfloor 180_y - \tau \rfloor$ is repeated N times to generate N spin echoes. The peak amplitude of successive spin-echo envelopes relaxes towards zero with an effective spin-spin relaxation time $T_{2e}$. If the noise components of the QR measurements are uncorrelated across echoes, then the average of the N coherent spin echoes has higher SNR than the measurement of any single spin echo.

The SLSE sequence $$90_x - \frac{\tau}{2} - [90_y - \tau]_N \qquad (1)$$

is similar to the CMPG sequence, except that the rephasing pulse has been shortened to $90_y$. In QR detection systems, the SLSE and CPMG sequences incorporate phase cycling in order to cancel spurious signals coherent with the RF pulses, such as ring down of energy in the probe coil and the DC offset from the receiver. The phase cycled CPMG and SLSE signals are represented as $$90_x - \frac{\tau}{2} - [180_y - \tau]_{\frac{N}{2}} - T_D - 90_{-x} - \frac{\tau}{2} - [180_y - \tau]_{\frac{N}{2}} \text{ and} \quad (2)$$

$$90_x - \frac{\tau}{2} - [90_y - \tau]_{\frac{N}{2}} - T_D - 90_{-x} - \frac{\tau}{2} - [90_y - \tau]_{\frac{N}{2}} \quad (3)$$

respectively. $T_D$ is the delay between successive sequences and −x indicates a 180°-phase change. FIG. 1a shows a diagram that represents both the phase cycled CPMG and SLSE sequences, for appropriate choices of the rotation angles θ and φ. Summing the first N/2 echoes and subtracting the last N/2 echoes forms an average QR response, after dividing by N. The delay $T_D$ is chosen on the order of the spin-lattice relaxation time ($T_1$) so that the quadrupolar nuclei have time to relax to their preferred orientation before the second set of N/2 echoes are acquired. The phase cycled SLSE and CPMG sequences are used in situations where it is not possible to attain a steady-state QR waveform in response to multi-pulse sequences, as is the case with TNT.

For other quadrupolar substances, such as RDX, it is possible to achieve a steady-state QR response between adjacent RF pulses using the SORC sequence:

$$[\theta_x - \tau -]_N, \quad (4)$$

where the rotation angle $\theta_x$ and pulse separation τ are chosen to maximize the steady-state waveform between adjacent pulses. Unlike either the CPMG or SLSE pulse sequences, which produce a spin echo midway between RF pulses, the SORC signal produces a spin echo centered on each pulse, as can be seen in FIG. 1c. The fundamental unit of the SORC sequence is the simplest of all sequences. The Free induction decay is shown following the pulse with a spin echo 180 degrees out of phase with the pulse, appearing after a delay of 2τ from the end of the previous pulse: after the first pulse a spin echo is obtained on every pulse, as shown in the sequence element in the figure.

The response, which appears in between successive pulses, represents the interference of the free induction decay and spin echo, following the leading pulse, with a spin echo centered on the trailing pulse. Interference can be constructive or destructive, depending upon the values of RF-pulse-frequency-offset from resonance (Δf) and τ. Constructive interference occurs when Δf, and τ satisfy: Δf(T)τ=n+½, where n is an integer and T indicates the dependence of frequency offset on temperature, with excitation and reception occurring at the same frequency. Contraband and other quadrupolar materials generally exhibit temperature dependence of quadrupole resonance frequency and this causes an equivalent dependence in Δf. For example, the transition frequencies for RDX have temperature sensitivity of approximately 500 Hz/° C. and within the expected maximum temperature range of roughly −40 to 50° C. this can easily shift Δf to severely limit or eliminate the absorption of incident RF energy by the quadrupolar nuclei of interest, and hence eliminate the QR response. As a result, in situations where the temperature of the target containing quadrupolar nuclei is not precisely known, it is not possible to choose the pulse spacing to satisfy the condition for constructive interference.

Figure 1B:
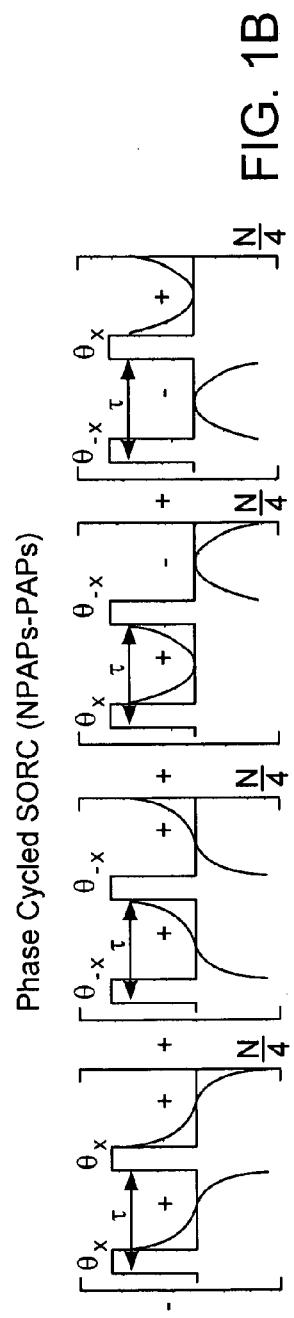
FIG. 1b illustrates one variant on the Phase cycled SORC (NPAPS-PAPS) sequence.
Figure 1C:
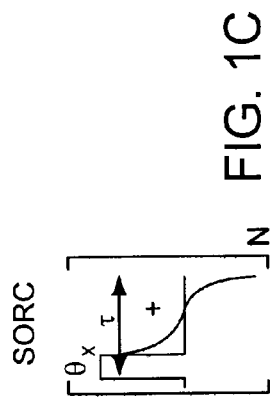
FIG. 1c illustrates the SORC sequence for QR detection systems.

A phase cycled SORC sequence can be used to cancel or severely attenuate the free induction decay signal and thereby reduce the sensitivity of the response to acoustic ringing and temperature variations, while also eliminating the DC offset of the receiver. The minimal phase cycled SORC sequence is constructed from two subsequences: a non phase alternated pulse sequence (NPAPS)

$$[\theta_x - \tau - \theta_x - \tau]_{\frac{N}{2}}$$

and a phase alternated pulse sequence (PAPS)

$$[\theta_x - \tau - \theta_{-x} - \tau]_{\frac{N}{2}}$$

to form the composite NPAPS-PAPs sequence $$[\theta_{-x} - \tau - \theta_{-x} - \tau]_{\frac{N}{2}} + [\theta_x - \tau - \theta_{-x} - \tau]_{\frac{N}{2}}, \quad (5)$$

which is equivalent to either the center two sequences or the two end sequences of FIGS. 1a, 1b and 1c, after accounting for differences in subsequence repetitions. Another variation on the phase cycled SORC sequence is constructed from four subsequences; two non phase-alternated pulse sequences and two phase alternated pulse sequences (PAPS) to form the composite NPAPS-PAPs sequence $$-[\theta_x - \tau - \theta_x - \tau]_{\frac{N}{4}} + [\theta_{-x} - \tau - \theta_{-x} - \tau]_{\frac{N}{4}} + [\theta_x - \tau - \theta_{-x} - \tau]_{\frac{N}{4}} + \quad (6)$$
$$[\theta_{-x} - \tau - \theta_x - \tau]_{\frac{N}{4}},$$

as shown in FIG. 1b. Operations within each subsequence, of addition or subtraction of responses, are indicated with a plus or minus sign centered on the response, whereas; operations between subsequences are indicated between them. Division of the sum by eight is required to form the average in this case, as the four subsequences each produce two responses.

The amplitude of the average QR signal obtained in multi-pulse sequences is sensitive to pulse sequence parameters such as $t_p$, τ and Δf. Because the optimum pulse parameters are determined by unknown factors such as the amplitude of the applied RF magnetic field at the quadrupolar nuclei and the temperature of the quadrupolar nuclei, one cannot obtain the maximum SNR for all regions by using a fixed set of pulse parameters. A method for using interlaced pulse sequences can use a range of pulse parameter values to lessen the effect of environmental uncertainties. In a preferred embodiment, measurements of the QR response, during sensing, are fed back to the system in real time, to automatically adjust the pulse parameters to improve the QR response.

The methods described for increasing the SNR of QR measurements also increase the search time. The present invention utilizes the fact that the throughput time of a QR detection system can be substantially reduced, while simultaneously increasing the number of QR signals obtained for averaging, by allowing the scanned object to move relative to the probe-sensing region, during the detection interval. The ability to detect scan-items containing quadrupolar nuclei that are moving in uncontrolled motion and with non-uniform velocity, relative to the probe-sensing region, during sensing is described in detail below.

Development of a practical, high throughput, QR detection system must consider the maximum speed at which the intended scan items will traverse the sensor. For example, the slowest speed a standard baggage conveyor operates at is about 2 miles per hour (0.6 kph), corresponding to about 3 feet per second (0.9 m/s), whereas; 6 miles per hour (9.6 kph), corresponding to about 9 feet per second (2.7 m/s), is faster than the standard baggage conveyor. Efficient implementation of the apparatus, without interrupting the normal flow of baggage, thus requires sensing with transit speeds of at least about 3 feet per second (0.9 m/s) and where speeds of about 9 feet per second (2.7 m/s) would be more than sufficient to address the range of expected conveyor speeds. This applies to accelerated motion, using the maximum speed achieved through the sensing region, upon exit. The present invention recognizes that motion of the scanned item imposes restrictions on the minimum size of the sensing region and the maximum time delay between successive pulses or pulse sequences, to enable at least one excitation and sensing operation, and preferably a plurality, as the item passes the sensing region. Practical limits may be placed on the maximum length of the sensing region, the minimum pulse separation, and the maximum scan-item velocity, in any particular application. Such operational limits may permit or negate QR detection of moving quadrupole nuclei, in a particular application. Limits which permit detection may allow trade-offs between 2 or more of the above parameters. In addition to these operational limits, other factors such as environmental variability, noise, and input power, as well as physical limits such as the resonance frequency of a particular material may further restrict operations. Specifically, temperature variations shift the resonance frequency of specific quadrupolar nuclei by an amount that is dependent upon the quadrupolar material. Additionally, although output response power is a function of many different variables for moving quadrupolar nuclei, its dependence on input power or magnetic field is not linear. Rather, output response power is a nonlinear function, exhibiting a substance-specific peak value as a function of average magnetic field at the nucleus. As a result, increasing input power may produce a decrease in output response power. Similarly, ambient noise variability may produce variable interference with signal response detection. All of these operational, environmental, and physical constraints on detection, and maximization, of the QR response can be accounted for during a calibration step that utilizes the predetermined parameters to adjust the response so as to maximize the initial output response.

In a preferred embodiment of the invention scan-items traverse the sensing region at speeds of at least 1 foot per second (0.3 m/s) and preferably greater than 2 feet per second (0.6 m/s), and most optimally between 3 feet (0.9 m) and 9 feet per second (2.7 m/s). $T_1$ for some common contraband targets, listed in Table 1, is measured in seconds. For a steady state pulse sequence, this means the length of the sensing region is at least 6 feet (1.8 m) for $T_1=2$ s and a 3 foot per second (0.9 m/s) conveyor. If the dimension of a single excitation or sensing coil, in the direction of transport, were 6 inches (0.2 m), excitation and/or sensing with the preferred pulse sequence is preferably completed in less than ⅙ second to enable at least one excitation and/or sensing operation during passage of the scan-item, for a conveyor operating at 3 feet per second (0.9 m/s). This example illustrates that time imposes a significant restriction on sensing, by eliminating all commonly practiced phase cycled sequences and even non-phase-cycled sequences in the steady state. In fact, any multipulse sequence applied to detection of moving quadrupolar nuclei cannot achieve a steady state if the scan-item traverses the sensing region in less than $T_1$. Practical applications therefore require maximizing signal amplitude in the shortest possible time and/or maximizing the length of the excitation and sensing regions in the transport direction, to maximize the number of excitation pulses and sensing measurements, assuming a fixed maximum velocity for scan items. For a fixed sensing region size, the maximum speed of a scan-item past the sensing region and the repetition rate of elemental pulse units will determine the number of responses measured. Multi-pulse sequences consisting of the shortest elemental unit provide the most responses. Multipulse sequences with non-constant phase pulses encounter difficulty when the target quadrupolar material is contained in a small volume of the scan item, and/or as velocity increases and/or the time separation between scan-items is small compared to the pulse sequence repetition time, and/or velocity is not constant during passage through the sensing region, in controlled or uncontrolled motion. Specifically, the response will become unpredictable if a scan-item moves into the sensing region and is subjected to a partial pulse-sequence upon exiting the sensing region. For example, a scan-item may contain a target quadrupolar material anywhere within its volume, entrance of the scan item into the sensing region does not guarantee entrance of the target material, unless the pulse sequence does not start until the entire scan-item is within the sensing region. Fundamental units from the CPMG and SLSE steady state sequences require a first pulse differing in phase from the subsequent pulse sequence, which is at least one pulse long, and usually much longer (see equations 1 and 2). SORC (FIG. 1c) requires the shortest fundamental unit consisting of a single pulse (see equation 5). Additionally, during motion across a single coil, unless there is a uniform magnetic field, the target excitation and response will vary in space and time, and with the motion producing a shifted signal. Successive pulse sequences within the sensing region, during motion, produce responses with variable phase shifts, which, if summed, result in degraded SNR, compared to a stationary sample. The combined action of motion-induced responses from partial pulse sequences and phase shifts is more severe in uncontrolled motion, owing to the greater unpredictability. Summation across multiple coils at different distances along the path can further degrade the result. Thus, there are time and space constraints placed upon the system by motion, which determine the maximum target speed or, speeds when more than one QR line is interrogated, the pulse sequence(s) that can be used, the processing that can be applied, and hence the possibility and quality of sensing. Existing systems have not addressed these constraints or identified how they can be integrated into the QR detection method and apparatus.

The present invention is designed to address uncontrolled motion including non-uniform velocity of the scan-item relative to the probe-sensing region during sensing. Should a scan-item remain stationary with respect to the probe-sensing region during sensing, the method still provides enhancement of the response by virtue of the fact that optimization for high speed enables more signals to be obtained per unit time than when this constraint is not present, and maximization of output response as a function of multiple input variables achieves improvement in SNR.

As referenced above, FIGS. 1a and 1b illustrate two types of pulse sequences used in QR detection systems. The phase cycled spin-locked spin-echo sequence (SLSE) or Carr-Purcell-Meiboom-Gill (CPMG) sequences are used to detect quadrupole materials that do not admit a train of steady-state QR waveforms in response to the applied RF pulses. The phase cycled strong off-resonant comb sequence, also known as PAPs-NPAPs (phase alternated pulse sequence (PAPs)-non phase alternated pulse sequence (NPAPS)) is used to detect quadrupole materials that admit steady-state QR waveforms in response to the applied RF pulse sequence.

For phase cycling to be effective, the phase shifts of superposing response components, which result from different parts of the excitation pulse sequence, preferably remains constant with respect to each superposing component, during the detection process, otherwise, the resulting QR waveforms can destructively interfere during signal averaging. The present invention recognizes that when a quadrupolar target is moving through the probe sensing region, during the detection process, consecutive QR responses, generated by multi-pulse sequences, will undergo motionally-induced phase rotations, causing the responses to sum incoherently in time. Motion-induced incoherent-summation and sensing-time limitations act individually and in combination to severely limit the utility of the SLSE and CPMG phase cycled pulse sequences, and eliminate the PAPs-NPAPs pulse sequence, when detection of moving quadrupolar nuclei is desired. SLSE and CPMG based transient pulse sequences can be implemented but these too can produce degraded responses due to response summation in the presence of motion induced phase shifts, responses from partial excitation pulse sequences, and sensing time limitations. Furthermore, as the instant when the scan-item first enters the probe sensing region is unknown in practice, and even more significantly, as the position of the quadrupolar target is unknown within a scan item, it is undesirable to use either the SLSE or CPMG based transient pulse sequences, which require the first pulse be applied as the target enters the probe sensing region. For example, if the target enters the probe sensing region before, or after, the first pulse of either the SLSE or CPMG sequence is applied, the remaining rephasing pulses will not result in the expected spin echo centered between rephasing pulses and summation will become unpredictable and dependent upon the timing of item entry into the probe-sensing region relative to the start of the pulse sequence. When sufficient responses can be obtained within the probe sensing region, as for example, when the scan item moves slowly through the probe, and/or when the fundamental pulse element provides a response in a time short compared to the time the scan item traverses the probe-sensing region, the deleterious effects mentioned above may not prevent detection via CPMG or SLSE based transient pulse sequences.

A feasible system of ensuring the expected coherent summation is to include a cueing method, which starts the pulse sequence after the scan-item is completely within the probe-sensing region, and with sufficient separation between successive items to prevent entry of items between pulse sequence starts. Scanning can terminate automatically after some maximum time, or, preferably, the end of scanning can be cued upon exit of the item from the probe-sensing region. Cued detection can be accomplished using an infrared, ultrasonic, laser, or other sensor to detect a scan-item entering, or entering and leaving, or preferably, completely within the probe-sensing region. Another alternative is a simple switch indicating when an item is completely within the sensing region, the switch being activated when the entrance, such as a door, closes. To minimize the length of the sensing region, and hence power consumption, the cross-section of the scan-item in the transport direction can be minimized by ensuring that the item is rotated so as to provide minimum cross section in the direction of transport, prior to entry into the sensing region. Such rotation can be accomplished automatically, as with a funneling type of mechanism in front of the entrance to the sensing region, manually, or automatically and manually, when necessary.

The operational complexity of CPMG or SLSE based transient pulse sequences can be avoided by using a SORC based transient pulse sequence. Because the pulses are all the same phase, cueing is not required and the pulse sequence can run continuously with the probe-sensing region being only that length required to achieve a minimum number of pulses for the desired output response. This length is shorter for SORC based transient pulse sequences than other pulse sequences, as the fundamental pulse sequence is shorter. The shorter sensing region also reduces power consumption. A SORC based transient pulse sequence is the preferred sequence for detecting moving quadrupolar targets, possibly concealed within larger opaque volumes.

Figure 2:
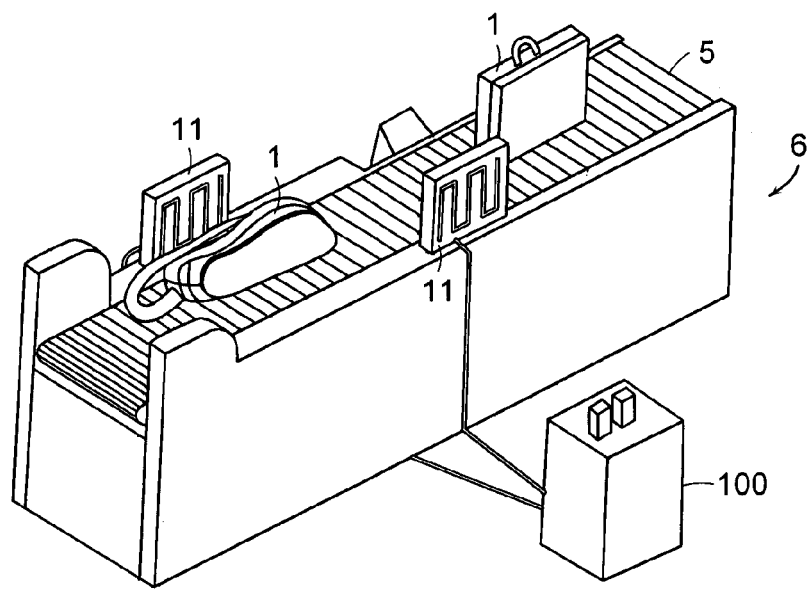
FIG. 2 illustrates a QR system for contraband detection within baggage, using a meander-line surface coil.

FIG. 2 illustrates a QR system that uses meander-line coils 11 to detect contraband within baggage 1 of transporter 6. A conveyor belts is used to position the baggage within the sensing region of a given meander-line coil.

Figure 3:
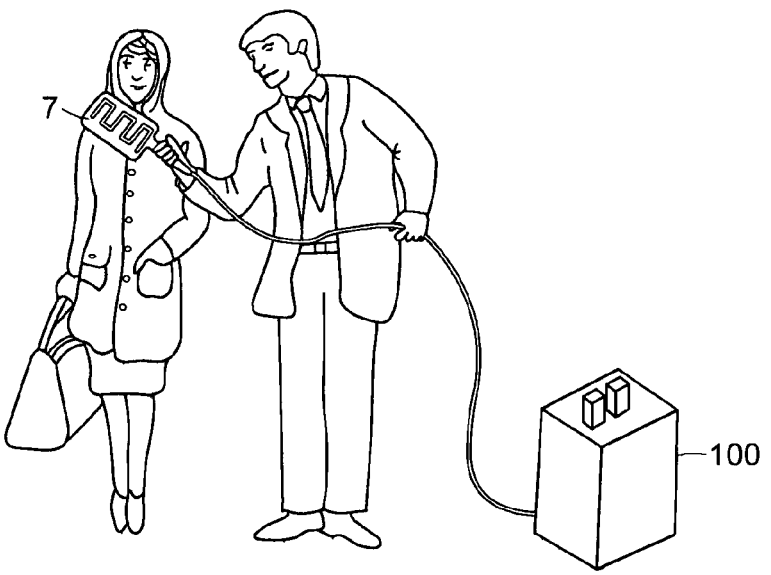
FIG. 3 illustrates a QR system for contraband detection of contraband on a human using a handheld meander-line surface coil.

FIG. 3 illustrates a QR system that uses a handheld probe 7 to detect contraband on a human. By using a handheld meander-line coil, for example, rather than a coil that surrounds the individual, significantly less power is needed to excite a QR response. In addition, because the RF magnetic field decreases exponentially from the surface of the meander-line coil, it is possible to excite a QR response without exposing the human to a large RF magnetic field.

Figure 4:
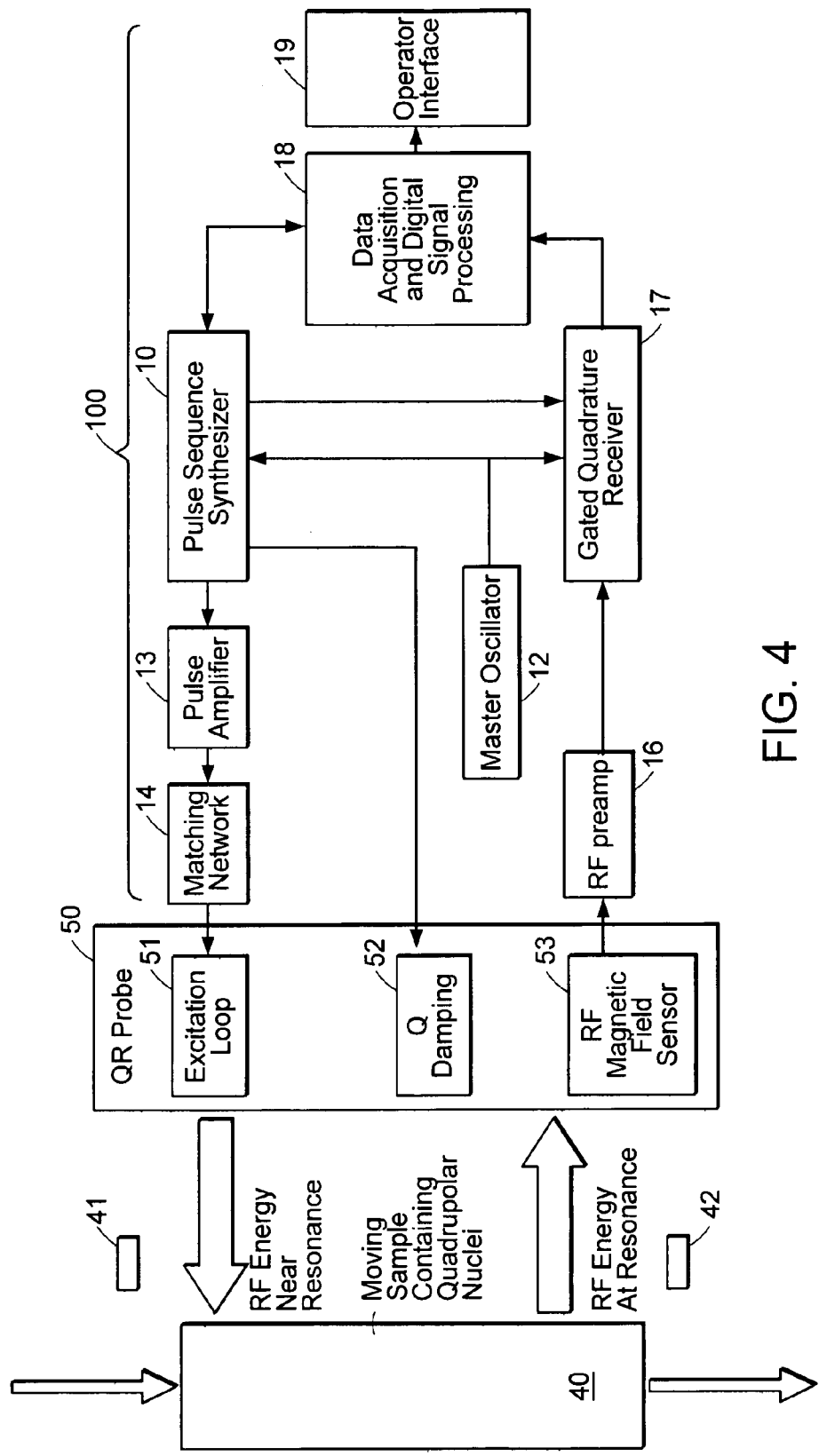
FIG. 4 illustrates a minimal system for detection of moving quadrupole nuclei in accordance with the present invention.

A system for detection of moving quadrupolar nuclei is shown in FIG. 4. The pulse sequence synthesizer 10 generates a train of RF pulses for exciting a QR response and controls the timing of events during the detection process. A master oscillator 12 provides a stable timing reference for the pulse sequence synthesizer. The pulse amplifier 13 boosts the amplitude of the RF pulses to a level sufficient for generating a QR response. The matching network 14 maximizes the transmission of RF power from the pulse amplifier to the QR probe 50, and is automatically tuned to account for variability of the electrical characteristics of the probe sensing region due to the presence of lossy materials or materials that significantly affect the relative permitivity of the space seen by the QR probe. The QR probe 50 includes an excitation loop 51 that produces the magnetic field for exciting a QR response in the moving scan-item within scan region 40, a Q Damping loop 52 that removes energy stored in the excitation loop and magnetic field sensor immediately following an RF pulse that can otherwise mask the QR response, and an RF magnetic field sensor 53 that detects the QR response. Input and output sensors 41, 42 can be used to trigger and end pulse sequence. The excitation loop and RF magnetic field sensor may be the same coil, or preferably, separate systems optimized for transmission of RF pulses and reception of QR responses, respectively. Coil geometries may be any that provide effective input signal and/or output response. The RF preamp 16 is a low-noise amplifier that boosts the QR signal before it is passed to a quadrature phase receiver 17.

The data processing, digital signal processing, and control system 18 digitizes the output responses, modifies the RF pulse sequence parameters to increase the output power and thereby increase the probability of correct detection while minimizing the probability of false alarm, and decides whether a quadrupole material is present, absent, or undeterminable, and controls the alarm. It may also control the motion of the conveyor or adjust its stopping and starring on an alarm. The status determination is accomplished by forming a scalar metric that represents the magnitude of the QR response, and then comparing this metric to a predetermined minimum-detection-threshold value. The operator interface 19 uses visual and audible signals such as a display to notify the operator when contraband is detected.

Figure 5A:
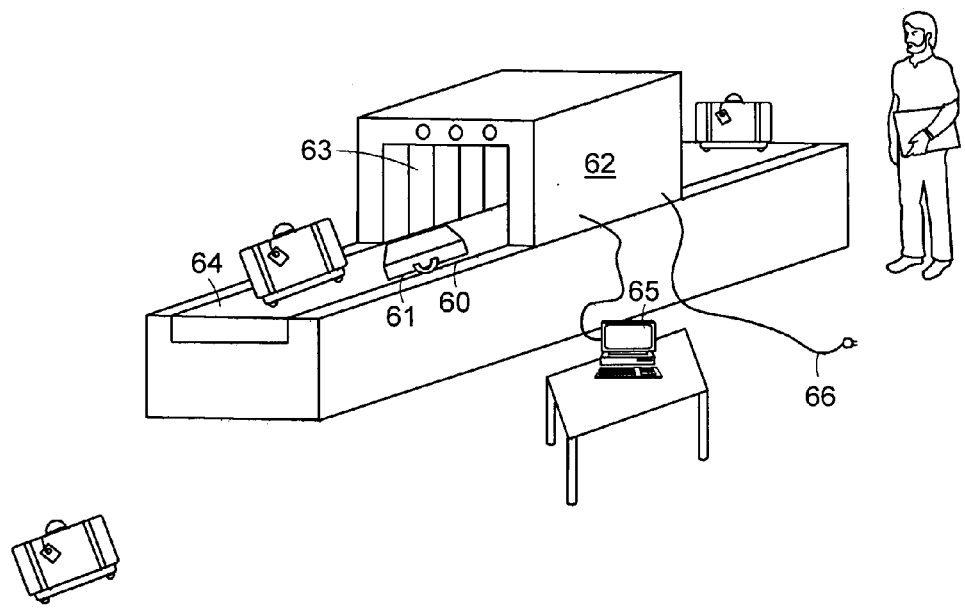
FIG. 5a illustrates a system for detection of contraband, within baggage, moving on a conveyor belt.
Figure 5B:
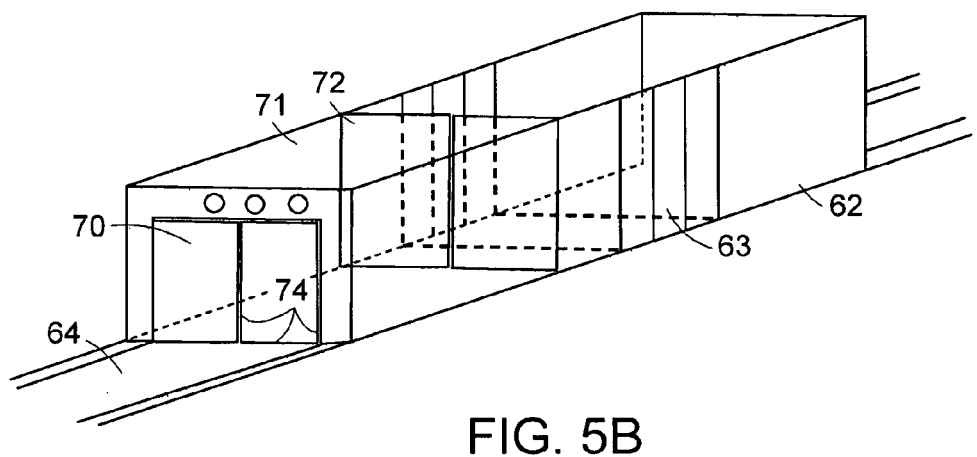
FIG. 5b shows a shielding system on one side of the probe-sensing region: symmetrical shields are located on the other side.
Figure 7:
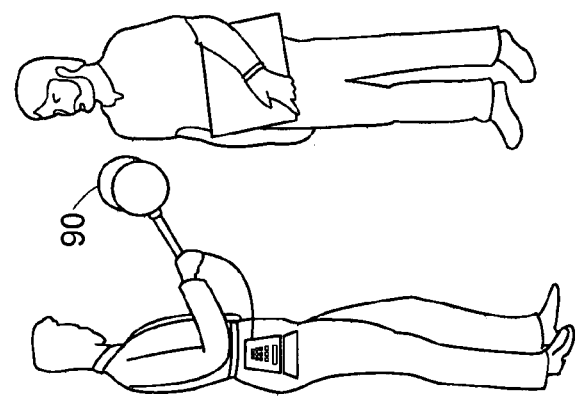
FIG. 7 illustrates a system for detection of contraband on a stationary human by sweeping a hand-held detector over the search region.
Figure 6:
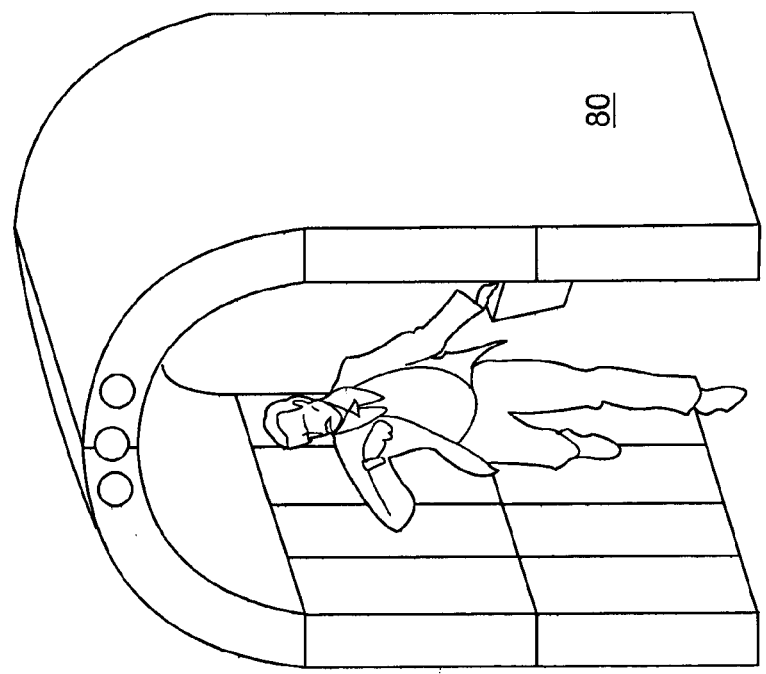
FIG. 6 illustrates a portal detection system for revealing the presence of contraband on moving humans.

FIGS. 5 through 7 provide examples of QR probe(s) used in preferred embodiments of the invention.

A system for detection of contraband within baggage moving on a conveyor belt is shown in FIG. 5a. A sealed container 60 transporting a concealed sample of a quadrupole substance 61, such as explosives, narcotics, biological weapons, or other quadrupole substances of interest, is shown in FIG. 5a, moving through a portal 62 containing one or more modular QR probes 63, arranged in an array. Excitation may use any geometry that facilitates sensing, however, a Helmholtz configuration disposed perpendicular to the transport direction is a preferred embodiment. The portal is designed to retrofit onto existing baggage conveyor belt systems, in which case the conveyor 64 is not controlled by the QR detection system, it does not operate at a constant speed, and its ends extend beyond what is shown in FIG. 5a, in a configuration representative of the specific facility. Shielding is integrated into the detection system with the QR probe(s) comprising the innermost chamber of the portal. Under low noise conditions, only one chamber may be required, with no exterior enclosure for noise reduction, as shown in FIG. 5a. Shielding components such as attenuative coatings, films, foams, and metals, are designed to fit onto the top and underside of the conveyor to attenuate RF noise that may be present due to the absence of shielding in the conveyor design. Data acquisition, processing and control of the system resides in the laptop computer 65, which also controls other system operations such as calibration, monitoring, and alarm, when necessary. In the event that noise cannot be attenuated sufficiently using the retrofit system, the system of FIG. 5a can also represent a stand-alone system where a purpose built conveyor 64 is controlled by the system through a laptop computer 65, which also controls other system operations such as calibration, monitoring, conveyor, and alarms, when necessary. The QR detection system is matched to the operational needs of the facility, outside of the scanning system. The conveyor may not be constant velocity. The conveyor is designed to minimize ambient noise by design integration with the probe chamber and the use of materials which minimize RF coupling from outside sources.

The detection process does not increase the transit time of containers as it occurs at the normal speed of the existing facility conveyor, or is matched to the facility logistics with the purpose built conveyor. The detection system is designed to excite a QR response using the smallest possible RF magnetic field amplitude so as to (1) avoid damaging the container contents such as sensitive electronic equipment and, (2) limit the excitation of spurious piezoelectric and magnetostrictive resonances. The detection system, through its shielding, excitation and sensing methods, and processing, also acts to limit reception of noise, in general, and external RF interference such as AM broadcasts, in particular. Power is supplied via the power cord 66.

A schematic representation of one shielding embodiment, within a chambered portal, is shown in FIG. 5b. The portal 62, QR probes 63, and conveyor 64 are the same as in FIG. 5a. When ambient noise requires additional shielding of the portal, a progressive reduction of ambient noise can be accomplished through shielding design that does not impede the flow. Specifically, the outer entrance is designed for maximum reflectivity of ambient RF sources to minimize passage of RF signals to the interior. This can be accomplished, for example, using swinging doors 70, in one embodiment. To further reduce any noise entering past the outer entrance, a second entrance 72 is disposed interior to the first with the chamber between the outer and first interior entrances 71, as well as the interior entrance facing the outer chamber 72, and the interior of the outer entrance 70, lined with material having a high attenuation coefficient for RF energy. The walls of the interior chamber 71 may be disposed at angles and in geometries that further facilitate the attenuation of RF energy propagating through the exterior entrance. Additionally, the distance between the exterior and interior entrances is such that the longest expected scan-item-dimension is completely contained within the chamber prior to entering the interior entrance. This will minimize the direct exterior radiation reaching the probe-sensing region 63. As all entrances will have seams 74 that radiate some energy into the interior, all seams are covered with flexible attenuative material to minimize radiation into the interior while permitting the operation of the entrances. This same shielding structure is disposed symmetrically about the probe sensing region to minimize RF noise in the innermost chamber 63. Multiple interior chambers 71 on each side of the probe sensing region 63 may be necessary to reduce the noise to acceptable levels, in situations where the ambient RF noise is significant.

A portal 80 containing an array of modular QR probes is placed within the path of mammal traffic without interrupting its normal flow, for example, human traffic within an airport is shown in the embodiment of FIG. 6. The modular array is arranged to excite a QR response from concealed quadrupole contraband, such as explosives, narcotics, biological weapons, or other materials of interest while the scan-item is moving through the portal. An array of Helmhotz pairs is a preferred embodiment with the Helmholtz coils disposed perpendicular to the average direction of transport. The detection system employs the smallest possible RF magnetic field amplitude to (1) reduce health risks to the mammal from the RF magnetic field and, (2) limit the excitation of spurious piezoelectric and magnetoacoustic resonances. The detection system also incorporates shielding, excitation, and response processing to limit reception of external RF interference such as AM broadcasts. Shielding may be incorporated into a room containing the portal to minimize the obstructions during traversal of the portal itself. In an alternative embodiment, the shielding is incorporated on the portal in a manner equivalent to that described in FIG. 5b for the baggage scanner, but with appropriate changes to fit the human portal.

A shielded hand held QR probe 90 is shown in FIG. 7 for detecting concealed quadrupole contraband materials on mammals or within sealed containers. The detection system employs the smallest possible RF magnetic field amplitude to (1) reduce health risks to the mammal from the RF magnetic field, (2) avoid damaging contents, such as sensitive electronic equipment, within containers, and (3) limit the excitation of spurious piezoelectric and magneto-acoustic resonances. The detection system also incorporates shielding, excitation and sensing, and processing of responses to limit reception of external RF interference such as AM broadcasts. Shielding for the handheld system is variable depending upon the class of items scanned. For example, flat objects incorporate an annular shield and a recessed coil for minimizing noise during motion. The shielding may be flexible to allow conformance to, and sealing of, the surface, thereby minimizing noise. Additionally, shielding may incorporate multiple chambers as discussed in FIG. 5b but with appropriate alterations to fit this configuration.

In each realization of the invention illustrated in FIGS. 5 through 7, the QR detection apparatus uses a multi-pulse sequence as described herein to improve the SNR of the QR measurement.

Figure 8:
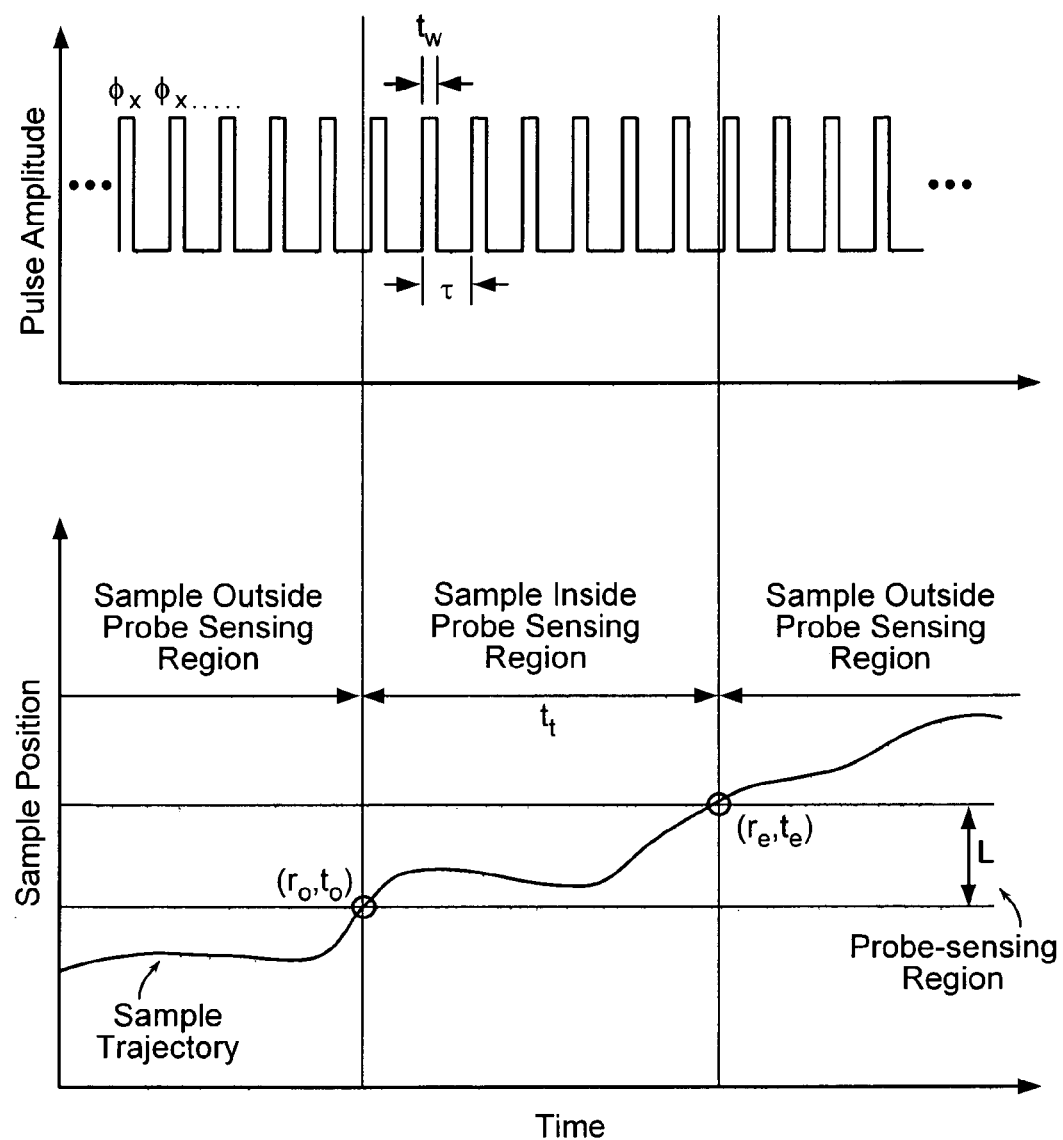
FIG. 8 illustrates transit optimized pulse sequence (TOPS) for detecting moving quadrupole nuclei.

FIG. 8 shows the timing of the applied RF pulses, which are a transient form of a constant phase SORC-type steady-state pulse sequence, and the trajectory of quadrupolar nuclei entering the probe-sensing region. In the most general case, the instant $t_o$ at which the quadrupolar nuclei enter the probe-sensing region is unknown. Furthermore, the transit time $t_t$ of quadrupolar nuclei through the probe-sensing region is also unknown, but may be extended by using multiple QR probes to expand the probe-sensing region. In most applications, it is possible to estimate the shortest target-transit-time across the probe-sensing region. This is accomplished by using the equation $t_{tmin}=L/S_{max}$ where $t_{tmin}$ indicates the minimum transit time, L is the linear dimension of the probe-sensing region in the direction of traversal, and $S_{max}$ is the estimated maximum linear speed. This estimate is conservative in that it approximates the target as a point cross-section in the transport direction, thereby minimizing its transit time: finite size objects will take longer to scan than the minimum estimated time and this may relax the sampling criteria slightly: finite size objects can be accounted for using $t_{tmin}=(L+d)/S_{max}$, where d is the smallest dimension of the target expected in the transport direction. The value of $t_{tmin}$ may place more or less stringent constraints on the pulse spacing, $\tau$, depending upon $t_{tmin}$, which in turn depends on the maximum target speed. For example, at a fast walking speed, of about 3.5 mph (5.6 kph), a person would traverse a half-foot (0.2 m) probe-sensing region in about 0.1 seconds.

Airport baggage conveyors move at between about 2 and 5 mph (3 and 8 kph), leaving roughly 0.07 seconds, at the highest speed, for measurement in the same probe. A mail sorting machine moves the mail at about 6.1 mph (9.8 kph), roughly twice as fast as a walking pace, leaving only about 0.05 seconds for completion of the sensing, within the same probe. Other applications may place more stringent requirements on the maximum scan time, if target speeds are higher. For example, sensing of buried mines while moving at 60 mph (96 kph) leaves only about 0.005 seconds for completion of the scan. In some case, $t_{min}$ may preclude sensing altogether by requiring a pulse spacing below any achievable. Alternatively, even when $t_{min}$ is achievable it may not be possible to attain sufficient signal enhancement, over a feasible sensing length, to provide reliable detection. Where feasible, $t_o$ can be defined by using a sensor to determine when an object is completely within the probe-sensing region, as described above.

In the general case where $t_o$ is unknown, it is recognized that neither the SLSE pulse sequence nor the CPMG, nor any of their phase cycled variants are applicable as it is not possible to determine when to apply the first 90° pulse. This is also true for the transient multipulse sequences based upon these steady state pulse sequences. In this case the TOPS sequence, a transient multipulse SORC based sequence, with output response maximized for motion, is employed. Furthermore, it is recognized that motion of the quadrupole sample relative to the probe-sensing region, during sensing, can introduce shifts between sequential QR responses. Such shifts degrade the coherent superposition of responses, which are the basis for noise attenuation in phase cycled pulse sequences, such as NPAPs-PAPs. Additionally, phase cycling is not desirable as it decreases the number of responses by increasing the time to acquire a response by at least a factor of 4 over SORC, and more commonly by at least a factor of 84 or much more. And so the preferred pulse sequence when there is uncertainty in the value of the arrival time $t_o$ is the SORC sequence.

In the specific case where $t_o$ can be independently determined, it is possible to use either the SLSE or CPMG sequence. However, as for the case of SORC, phase cycling is not desirable as motion causes shifts of sequential responses and these shifts degrade the coherent superposition of responses, which are the basis for noise attenuation in phase cycled pulse sequences. Additionally, phase cycling is not desirable as it decreases the number of responses by increasing the time to acquire a composite response by more than the ratio of $t_D/\tau$, where $t_D$ is the delay between phase cycles, usually about $T_1$ and $\tau$ is the SORC pulse operation. The result is that motion severely degrades or eliminates the ability of phase-cycled sequences to attenuate coherent noise: depending upon the relation between the start of a phase-cycled sequence and time from entry to exit of the target, it is possible that phase cycled sequences will even produce a response having noise components significantly enhanced compared to the response from a single pulse.

Figure 9:
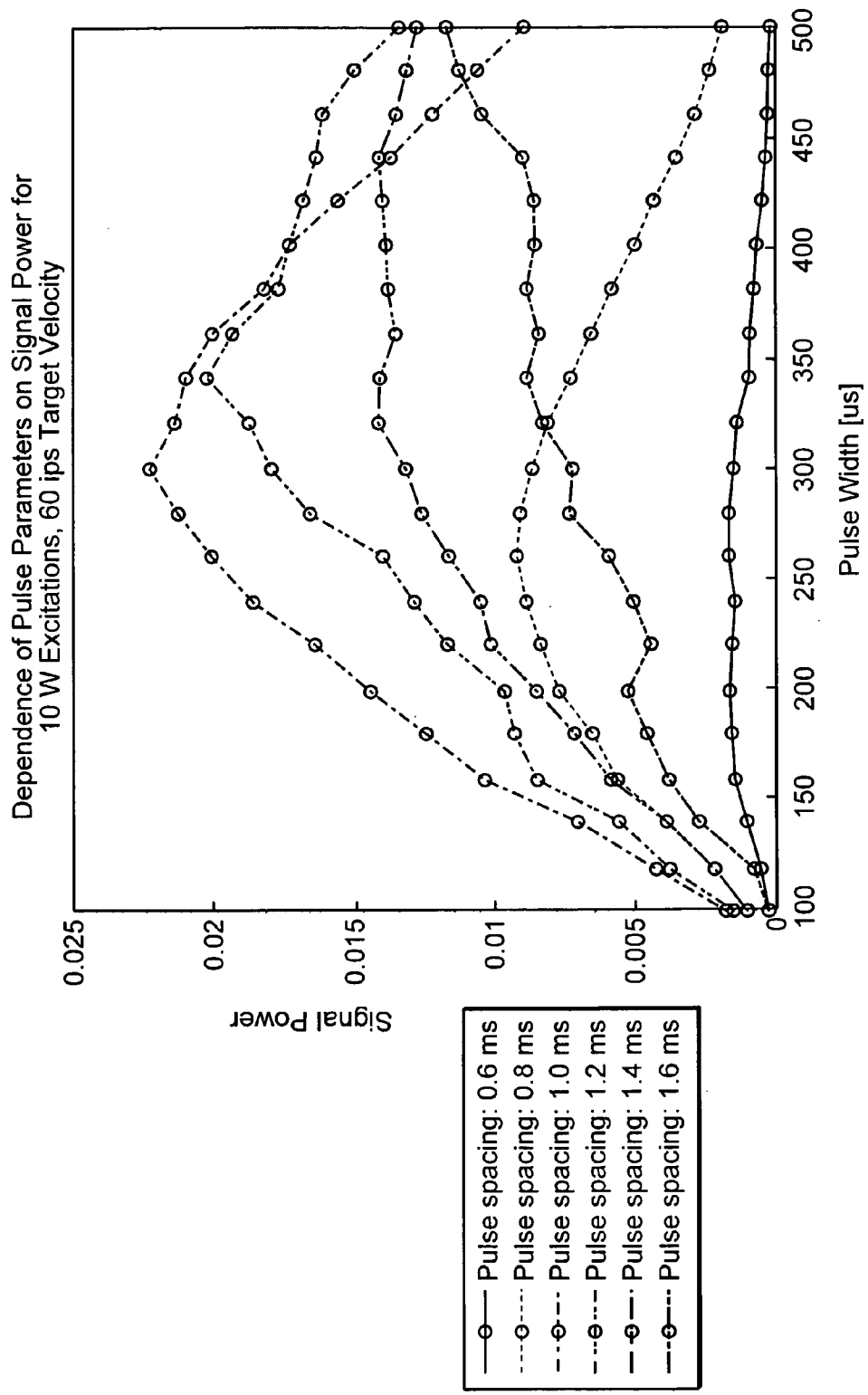
FIG. 9 illustrates the effect of pulse parameters on the QR response from a moving scan-item.

Minimum transit time constraints, imposed by the target maximum speed, minimum cross-section in the transport direction and the dimension of the probe sensing region, by themselves, favor the shortest possible pulse spacings, t, to maximize SNR. However, optimization of r based upon these constraints may not achieve an optimal QR signal, or even a measurable signal, without prior optimization of the measurement system. Independent of the pulse sequence used, it is necessary to optimize $t_p$, $\tau$, $\Delta f$, and RF pulse amplitude ($A_p$) to maximize the amplitude of the QR response, as demonstrated by FIG. 9, for the SORC pulse sequence. FIG. 9 shows the variation of the SORC signal power with respect to the pulse width and for different pulse separations while maintaining a fixed excitation frequency, pulse amplitude, and sample velocity. Note that a unique set of pulse parameters maximizes the received SORC signal power. In general, the optimizing values of the pulse parameters are unknown prior to the measurement because of imprecise knowledge of the trajectory, size, and temperature of the quadrupolar nuclei.

The preferred method for optimizing pulse parameters is to use measurements of the QR signal to guide tuning of the pulse parameters using a feedback optimization procedure. The feedback process, and more importantly, the process sequence used to decide the presence or absence of quadrupolar nuclei, requires calculation of a metric of the QR response quality. Examples of such metrics are peak-to-peak signal amplitude, signal energy, and signal power.

Recognizing that passage of the quadrupolar target through the probe sensing region produces a shift across successive SORC responses, averaging SORC waveforms in the time domain does not yield an optimal SNR, as illustrated in FIGS. 10a and 10b. FIG. 10 shows the in-phase and quadrature components of the receiver output in the upper (FIG. 10a) and lower (FIG. 10b) plots, respectively. The solid (red curve) represents the average SORC waveform obtained for a quadrupolar target with 14% fill factor that is stationary in the center of the probe-sensing region. The dashed curve (green curve) shows the average of all SORC waveforms acquired before, during, and after passage of the same target through the same probe with uniform target acceleration of approximately 32 feet per second squared (9.8 m/s$^2$), with a velocity of approximately 12 mph (19 kph) in the center of the probe sensing region. In comparison to the case of the stationary target, the moving target clearly shows a significant degradation of the composite response. Averaging only waveforms acquired when the moving quadrupolar target is within the probe-sensing region yields the dotted (blue curve). Compared to the stationary target, this composite response is also degraded and clearly shows a lower frequency and lower amplitude caused by shifting the individual responses that comprise the composite. As a result, time-domain superposition produces only a minor improvement in the SNR.

Figure 11A:
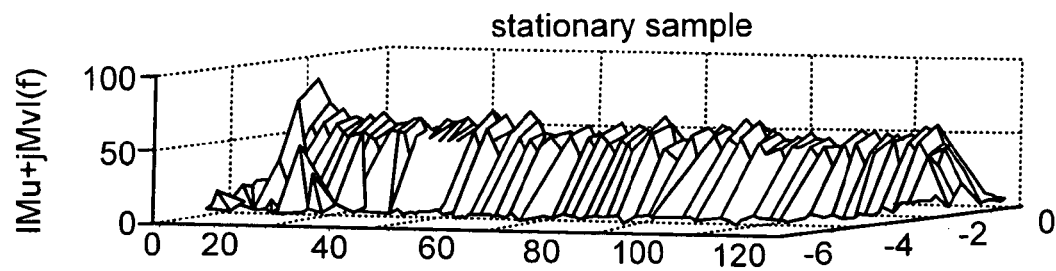
FIGS. 11a, 11b and 11c illustrate a comparison of quadrupole signals in the frequency domain from a stationary quadrupolar target with fill factor 14%, and the same target moving at 12 mph (19 kph) through the probe sensing region.
Figure 11B:
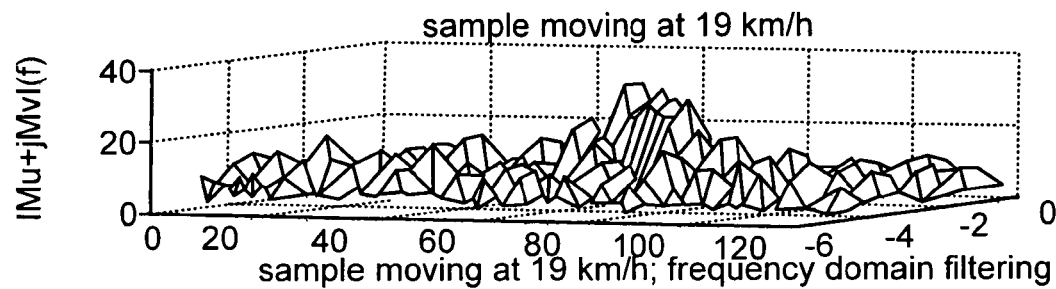
Figure 11C:
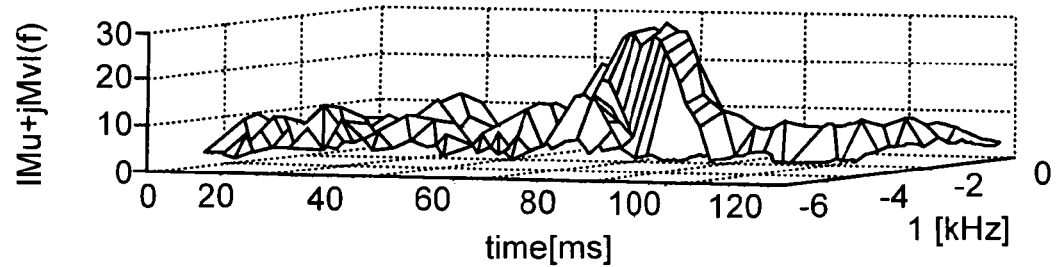

In order to avoid destructive interference due to shifting of responses from successive SORC pulses, an average QR signal is formed from the magnitude of the Fourier transform for each SORC waveform as illustrated in FIGS. 11a, 11b and 11c. The vertical axis represents the magnitude of the frequency response of the QR waveform recorded at the time indicated by the time axis. The upper plot (FIG. 11a) shows the QR response from a quadrupolar sample fixed within the center of the probe sensing region, while the middle plot (FIG. 11b) shows the response from a sample with 14% fill factor moving with uniform acceleration of 32 feet per second squared (9.8 m/s$^2$) through the probe sensing region, with a velocity of approximately 12 mph (19 kph) at the center of the probe sensing region. The SNR of the QR frequency domain response is improved by applying a moving average filter in the frequency domain across the time axis to obtain the smoothed spectral response shown in the lower plot of FIG. 11c. Several signal metrics can be derived from the smoothed spectra, including peak value and the volume of the region where the spectrum is 3 dB down from its peak value.

Figure 12:
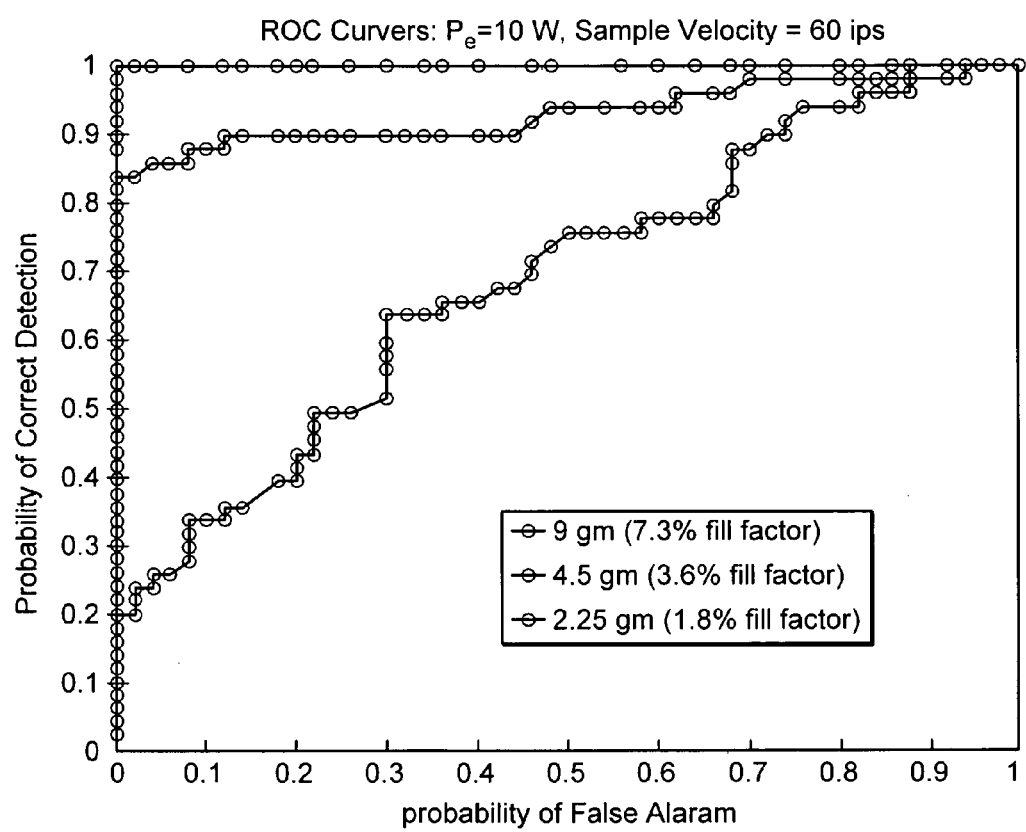
FIG. 12 illustrates ROC curves obtained using 10 W excitation and a target velocity of 3.4 mph (5.5 kph) for three different target sizes corresponding to fill factors of 1.8%, 3.6%, and 7.3%.

The performance of a QR detection system is quantified by a receiver operating characteristic (ROC) curve that shows the probability of correct detection (PCD) and corresponding probability of false alarm (PFA) for a given value of the detection threshold. FIG. 12 shows ROC curves that were experimentally determined by performing a series of one hundred experiments. In each experiment a sample was accelerating through the probe sensing region at 32 feet per second squared (9.8 m/s$^2$), and the velocity of the sample at the center of the probe sensing region was approximately 3.4 mph (5.5 kph). In the first fifty experiments the sample contained no quadrupole nuclei, while in the second fifty experiments the sample contained quadrupole nuclei. For each experiment a metric of the QR response was calculated and normalized so that the largest observed metric is unity. A single ROC curve is constructed by varying the decision threshold form 0 to 1 in steps of 0.01, and for each decision threshold calculating the probabilities of correct detection and false alarm. Three ROC curves are shown for three different target sizes corresponding to fill factors of 1.8%, 3.6%, and 7.3%.

FIGS. 13a, 13b, 14a and 14b describe different preferred embodiments of the present invention. The steps up to and including removal of the DC offset are the same for each: they are described here once. At the start of operation the matching network is adjusted to maximize the transfer of power to the probe. A calibration sample is passed through the probe sensing region at the maximum expected speed and the system automatically adjusts the matching network and optimizes pulse parameters ($\tau$, tp, $A_p$, and $\Delta f$) in TOPS to maximize the SNR per unit time and minimize the required RF pulse amplitude. It is understood that the TOPS is a preferred embodiment, however, other pulse sequences, such as those previously described may be used under appropriate circumstances, which are more restrictive than those to which TOPS applies. The probe sensing region is then continuously irradiated using TOPS while people, baggage, and/or other containers traverse it. During this period the system continuously adjusts the matching network to account for changes in the electrical characteristics of the probe sensing region, and varies the TOPS parameters around the nominal values obtained from the calibration sample in order to account for variations in target temperature and motion of the target with respect to QR probe(s) within the probe sensing region. It is understood that under favorable circumstances where the QR response is robust to changes in operational and environmental parameters, the real time adjustment may be reduced or eliminated. Measured QR responses are stored to some media such as a computer disk or memory and processed first by removing a DC offset component.

Figure 13A:
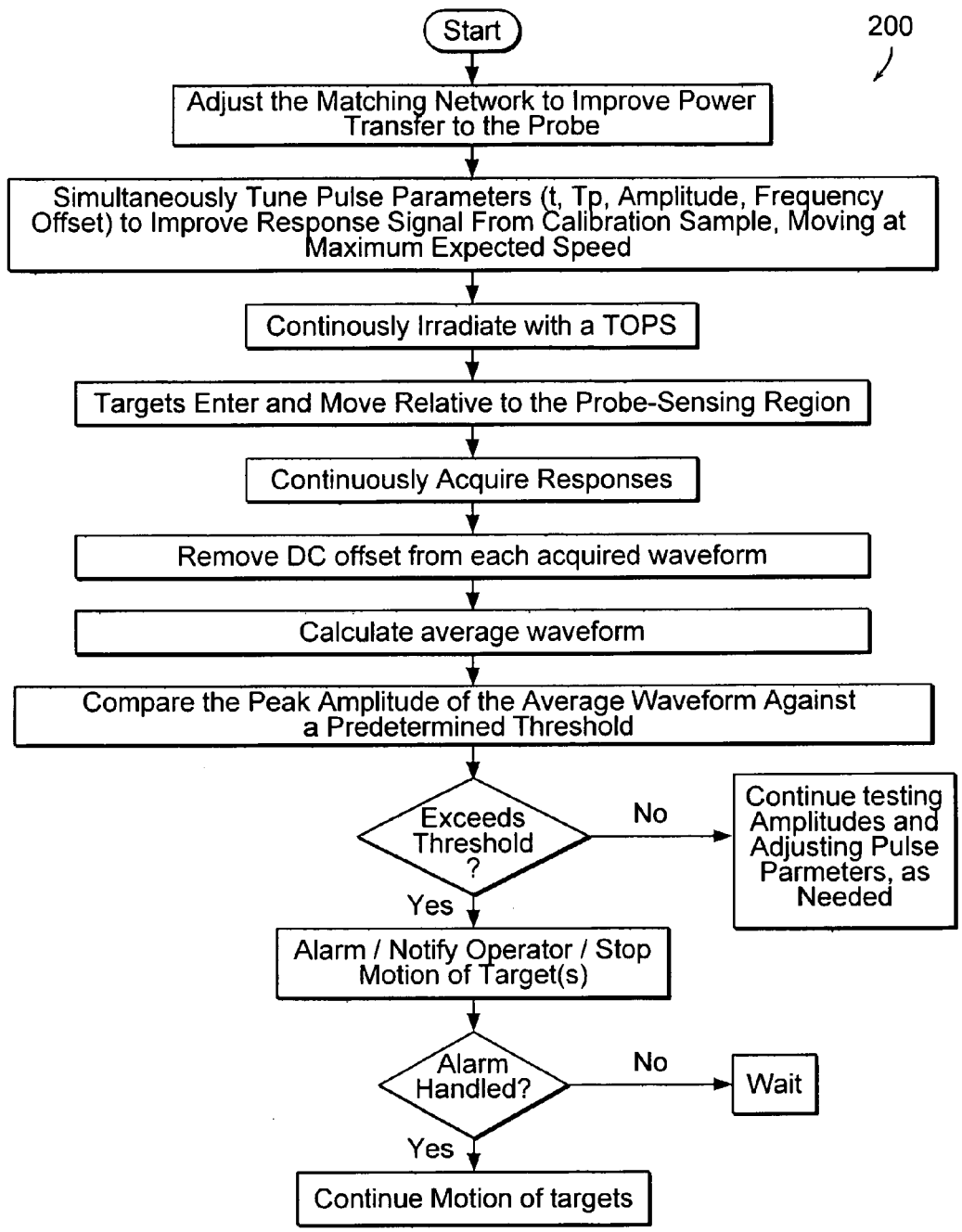
FIGS. 13a and 13b are process flow diagrams in accordance with a preferred embodiment of the present invention.

FIG. 13a shows a flow chart describing a preferred process 200 of the present invention, under conditions where the motion-induced phase shifts are small enough that time domain averaging of responses produces a significant enhancement of the signal, without having to resort to the frequency domain. Under such circumstances, the time domain has the advantage of speed as no transformation is necessary prior to summation. Averaging QR responses in the time domain is followed testing for a signal above the predetermined threshold level: exceeding the threshold produces an alarm and stops the motion of scan-items until the alarm is resolved, otherwise; averaged amplitudes of QR responses continue to be tested and continuous update of the parameters, using the signal metric is performed, as necessary.

Figure 13B:
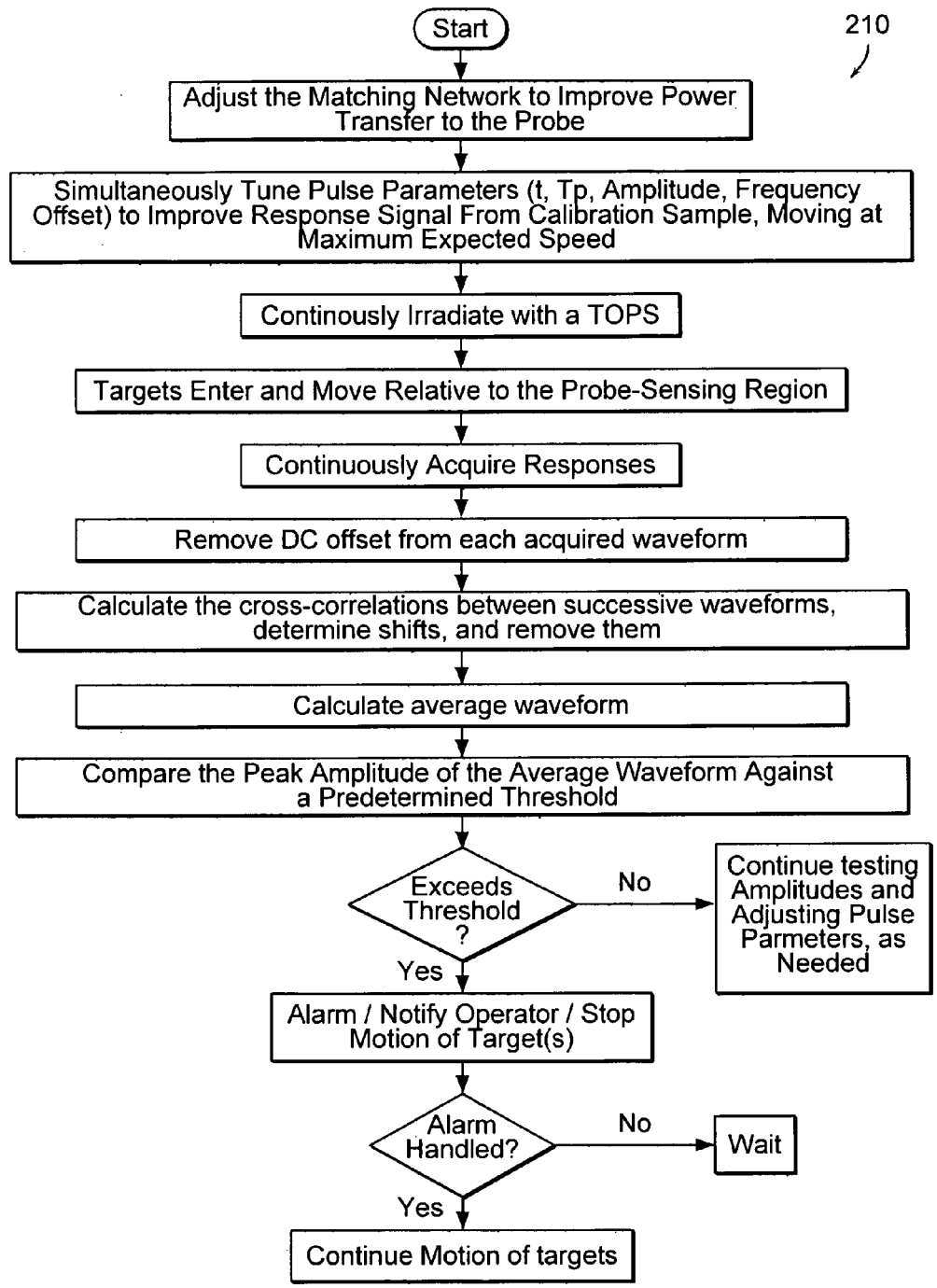

When motion induced affects are more severe, and simple time domain addition does not produce an enhanced result, cross-correlation of waveforms in the time domain can be used, as described in the flow chart 210 of FIG. 13b, however; reliable shift determination from cross-correlation of individual time-domain responses requires a SNR greater than a threshold value: for large signals this may be viable but it is unlikely to be reliable across the potential spectrum of expected signal sizes. Following correction of shifts determined by the cross-correlation, summation and testing proceeds as in FIG. 13a.

Figure 14A:
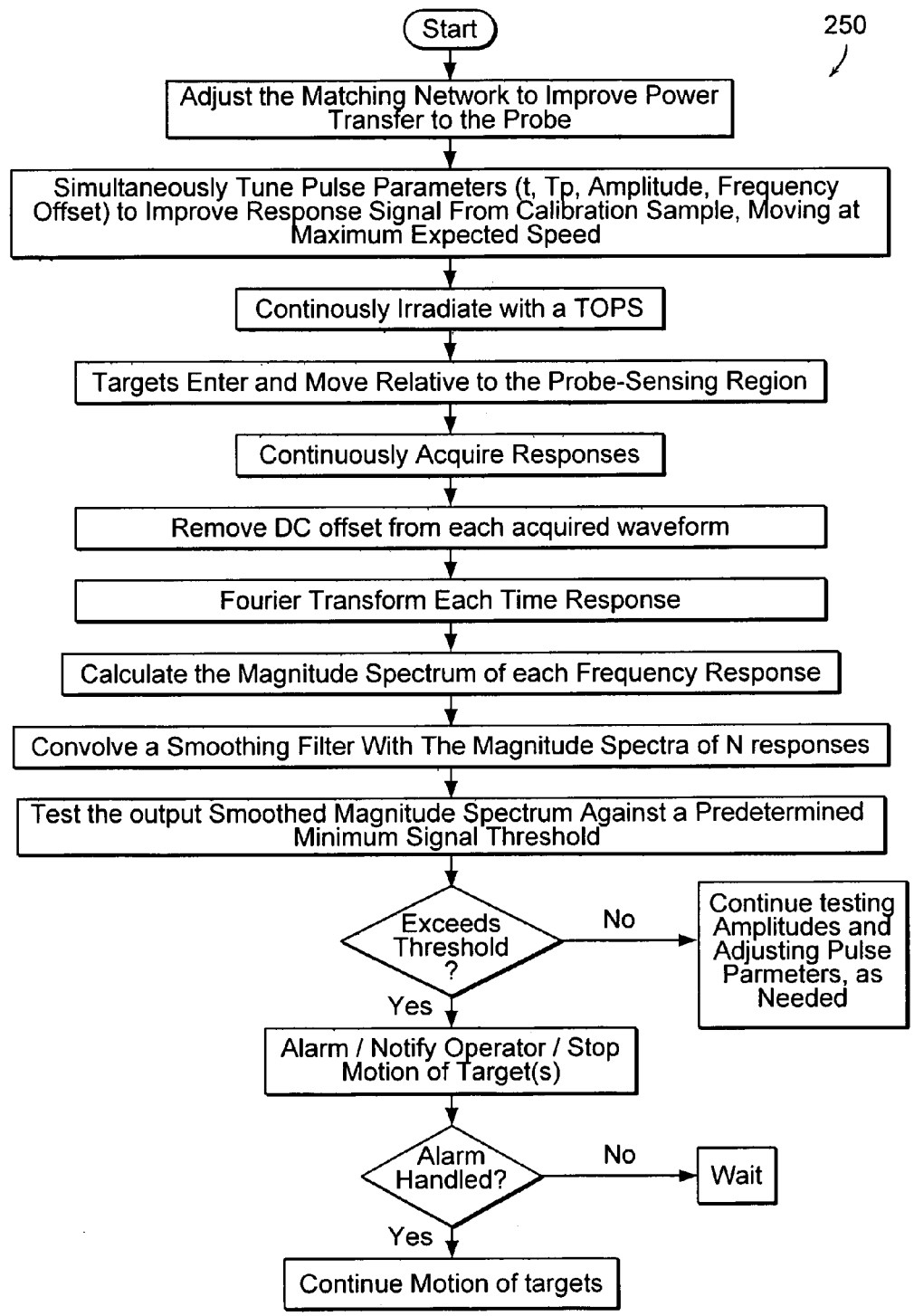
FIGS. 14a and 14b are process flow diagrams of a preferred embodiment of the invention.
Figure 14B:
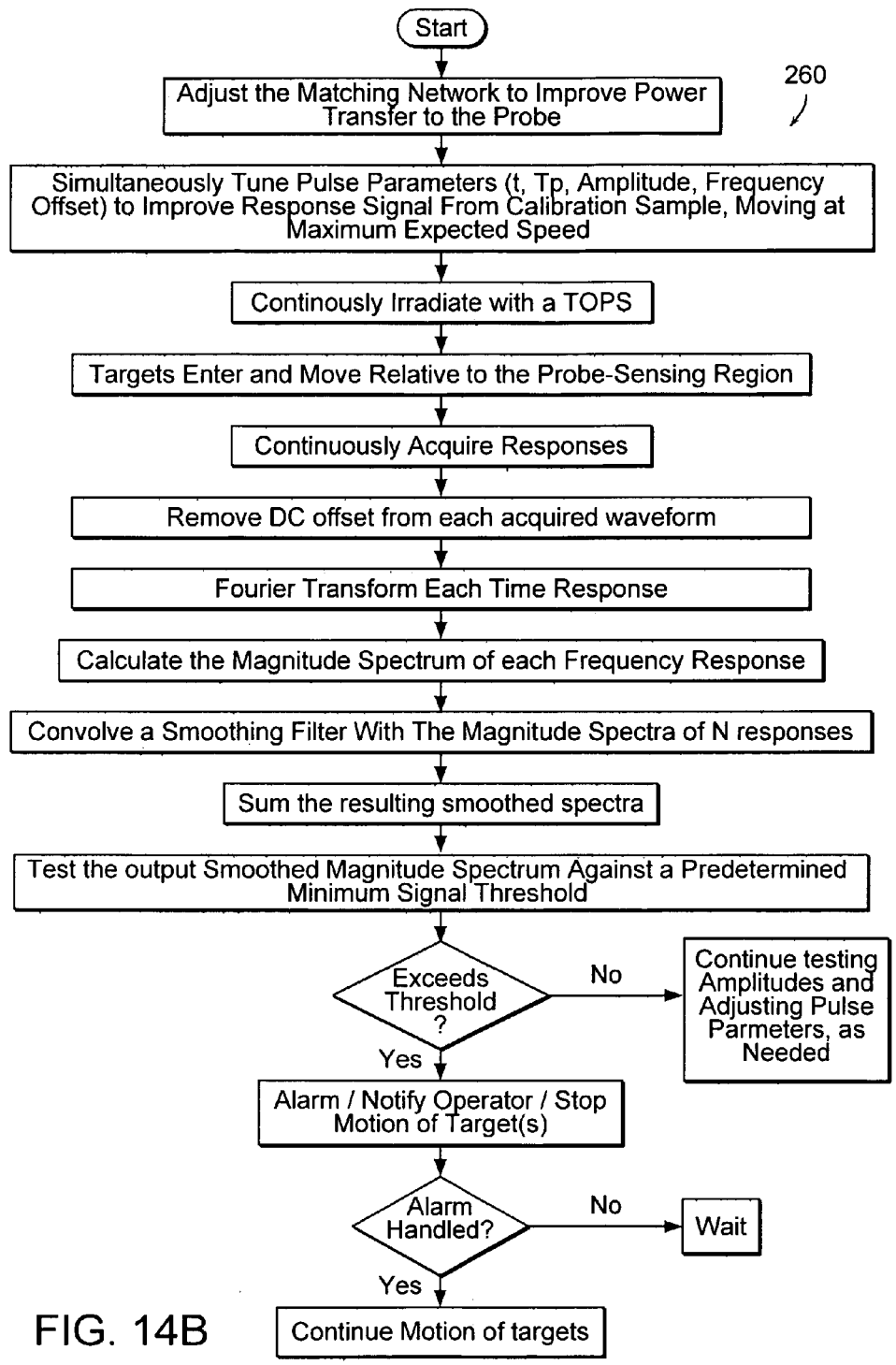

The most preferred embodiments of the present invention accomplish summation of motionally shifted QR responses in the frequency domain. Discarding phase information allows superposition of the spectral responses and identification of the QR response characteristic of a particular quadrupolar material. FIGS. 14a and 14b show flowcharts describing additional preferred embodiments of the present invention.

Calculation of magnitude spectra 250 for zero mean QR responses follows removal of DC offset, in FIG. 14a. Processing to attenuate AM, piezoelectric, and magnetoacoustic noise components can be applied, if necessary. This can be achieved by using standard filtering methods, applied with the appropriate filter-response selected based upon the noise characteristics. The preferred method is achieved by filtering the magnitude spectra to remove spectral components outside the QR response frequency range. SNR enhancement is applied using N consecutive spectra and convolving with a smoothing filter to form a smooth spectral response from which a signal metric is derived. N will depend upon the signal, noise, and maximum speed of the scan-item through the probe-sensing region. Values of N less than ⅓ the total number of scans collected when a target traverses the probe-sensing region at maximum speed are preferred. Smoothing of QR responses in the frequency domain is followed by testing for a signal above the predetermined threshold level: exceeding the threshold produces an alarm and stops the motion of scan-items until the alarm is resolved, otherwise; smoothed magnitude spectra of QR responses continue to be tested and continuous update of the parameters, using the signal metric is performed, as necessary. The smoothed spectra are not used individually but rather summed 260 to produce a single spectrum in FIG. 14*b*. Comparing of the smooth spectra against a reference is then performed in 14*a*.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method for scanning objects comprising:
   performing a non-phase-cycled excitation-pulse-sequence;
   adjusting a response to a given quadrupolar substance by calibrating said response to a set of predetermined operational parameters, at least one of the parameters being selected from the group consisting of the pulse separation, $\tau$, the pulse width $t_p$, the frequency offset, $\Delta f$, the ambient temperature, T, the maximum velocity expected for said scan-item passing through said probe-sensing-region, $v_{max}$, the length of said probe-sensing-region, L, and the resonance frequency of the quadrupolar nuclei, $\omega_r$;
   scanning an object in relative motion with respect to a probe-sensing region, and passing through said probe-sensing region, during sensing; and
   processing the response to said excitation-pulse-sequence and forming an output-response that indicates a characteristic of the object.

2. The method of claim 1 further comprising obtaining a plurality of quadrupole resonance responses.

3. The method of claim 2 wherein said output response is formed by superposition of responses in the time domain.

4. The method of claim 2 wherein said output response is formed by cross-correlation of successive responses and correction of lag, prior to superposition in the time domain.

5. The method of claim 2 wherein said output response is formed by superposition of frequency domain magnitude responses of successive scanned object responses.

6. The method of claim 5 wherein said output response is formed by superposition of frequency domain magnitude responses after low-pass filtering across individual magnitude spectra at the frequency-offset axis.

7. The method according to claim 1 wherein said non-phase-cycled pulse sequence comprises a CPMG sequence.

8. The method of claim 1 wherein said relative motion is uncontrolled comprising cueing the start of said excitation pulse sequence.

9. The method of claim 1 wherein said relative motion is controlled comprising cueing the start or end of said excitation pulse sequence.

10. The method of claim 1 wherein said processing comprises an iterative update of the predetermined operating parameters to adjust the response during the scan.

11. The method of claim 10 wherein said iterative update comprises a plurality of responses.

12. The method of claim 1 wherein said output-response is formed by superposition of updated responses in the time domain.

13. The method of claim 1 wherein said output-response is formed by cross-correlation of successive responses and correction of lag, prior to superposition in the time domain.

14. The method of claim 1 wherein said output-response is formed by superposition of frequency domain magnitude responses of successive scan-item responses.

15. The method of claim 1 wherein said output-response is formed by superposition of frequency domain magnitude responses after low-pass filtering of individual magnitude spectra at the frequency-offset axis.

16. The method of claim 1 wherein said output-response (s)-dependent cue comprises and audio, visual, or a sensory stimulus.

17. The method of claim 1 wherein said non-phase-cycled pulse sequence comprises a SLSE sequence.

18. The method of claim 1 wherein said non-phase-cycled pulse sequence comprises a TOPS sequence with constant phase pulses.

19. A method for scanning objects comprising:
    scanning a moving object with a first pulse sequence;
    detecting a first quadrupole resonance (QR) signal in response to the first pulse sequence;
    modifying pulse parameters from the first pulse sequence to form a second pulse sequence;
    scanning the moving object with the second pulse sequence;
    detecting a second QR signal in response to the second pulse sequence; and
    processing the detected signal to determine a characteristic of the object.

20. The method of claim 19 further comprising providing a system controller to provide timing signals and programming signals to a pulse sequence synthesizer.

21. The method of claim 19 further comprising providing a plurality of transmission probes and a plurality of receive probes.

22. The apparatus of claim 21 further comprising a transporter that moves the object being scanned with uncontrolled motion such that the object undergoes an acceleration within the scanned region.

23. The method of claim 19 wherein the pulse parameter are selected from the group consisting of pulse spacing, pulse length, offset from a resonance peak, and pulse power.

24. A method of detecting quadrupolar material during scanning of an object comprising:
    applying a pulse sequence to a scanning region, the object undergoing relative motion with respect to a transmitter;
    detecting a response of the object to the pulse sequence to provide a response output signal;
    separating magnitude data and phase data in the output signal; and
    processing the magnitude data to detect quadrupolar material in the object.

25. The method of claim 24 further comprising performing a fourier transform on the output signal.

26. The method of claim 24 further comprising applying a plurality of pulse sequences to the object to form a plurality of response output signals.

27. The method of claim 26 further comprising separating the phase data and magnitude data for each of the plurality of response output signals and summing the magnitude data from the plurality of response output signals.

28. The method of claim 26 further comprising averaging the magnitude data.

29. The method of claim 26 wherein the plurality of pulse sequences have a constant phase.

30. The method of claim 26 wherein the pulse sequences have both constant and variable phase.

31. The method of claim 24 further comprising detecting the entry of the object into the scanning regions with a sensor and initiating a first pulse sequence in response to the sensor.

32. An apparatus for scanning objects comprising:
a source coil that applies a pulse sequence to a scanning region;
a sensor that detects entry of an object to be scanned into the scanning region;
a receiver coil that detects a quadrupole response in an object undergoing relative motion to the source coil in the scanning region; and
a processor having a stored program that initiates application of a pulse sequence and that processes detected the response.

33. The apparatus of claim 32 wherein the transport mechanism is an external component and is uncontrolled by the scan system.

34. The apparatus of claim 32 wherein the transport mechanism is an internal component and is controlled by the scan system operating at a speed having a steady state pulse sequence.

35. The apparatus of claim 32 wherein the shielding enclosure comprises one or more enclosures that reduces RF noise while transporting objects to be scanned through a scan region.

36. The apparatus of claim 32 wherein the sensor is connected to a controller that initiates a pulse sequence in response to the sensor.

37. The apparatus of claim 32 further comprising a transport mechanism that transports the object through the scanning region.

38. The apparatus of claim 32 wherein the source coil further comprises a handheld probe.

39. The apparatus of claim 32 further comprising a shielding enclosure.

40. The apparatus of claim 32 further comprising a pulse synthesizer and a clock.

41. The apparatus of claim 32 further comprising a pulse amplifier.

42. The apparatus of claim 32 further comprising a matching network.

43. The apparatus of claim 32 further comprising a Q damping element.

44. The apparatus of claim 32 further comprising an RF magnetic field sensor.

45. The apparatus of claim 32 further comprising a gated quadrature receiver.

46. The apparatus of claim 32 wherein the processor is programmed to perform a fourier transform on an output signal and to separate phase data and magnitude data.

47. The apparatus of claim 32 further comprising a low pass filter.

48. The apparatus of claim 32 wherein the processor adjusts scan parameter of an object during a scan.

49. The apparatus of claim 32 further comprising a display that displays a response characteristic of an object being scanned.

50. The apparatus of claim 32 wherein the object has a speed of at least 3 kph.

* * * * *